United States Patent [19]

Adams et al.

[11] Patent Number: 5,276,149
[45] Date of Patent: Jan. 4, 1994

[54] 2-(N-IMIDAZOLIUMPHENYL)-CARBAPENEMS

[75] Inventors: Alan D. Adams, Piscataway; James V. Heck, Scotch Plains, both of N.J.

[73] Assignee: Merck & Co., Inc., Rahway, N.J.

[21] Appl. No.: 777,948

[22] Filed: Oct. 17, 1991

[51] Int. Cl.$^5$ .................. C07D 489/04; A61K 31/40
[52] U.S. Cl. .................................................. 540/302
[58] Field of Search ........................................ 540/302

[56] References Cited

U.S. PATENT DOCUMENTS

| | | | |
|---|---|---|---|
| 4,260,627 | 4/1981 | Christensen et al. | 424/274 |
| 4,465,632 | 8/1984 | Christensen et al. | 260/245.2 |
| 4,543,257 | 9/1985 | Cama et al. | 514/210 |
| 4,729,993 | 3/1988 | Christensen et al. | |
| 4,775,669 | 10/1988 | Cama et al. | |
| 4,962,101 | 10/1990 | DiNinno et al. | |
| 4,978,659 | 12/1990 | DiNinno et al. | 540/302 |
| 5,004,739 | 4/1991 | Salzmann et al. | |
| 5,004,740 | 4/1991 | Salzmann et al. | |
| 5,006,519 | 4/1991 | DiNinno et al. | |
| 5,011,832 | 4/1991 | Salzmann et al. | |
| 5,025,006 | 6/1991 | Salzmann et al. | |
| 5,025,007 | 6/1991 | Greenlee et al. | |
| 5,025,008 | 6/1991 | DiNinno et al. | |
| 5,032,587 | 7/1991 | DiNinno et al. | |
| 5,034,384 | 7/1991 | Greenlee et al. | |
| 5,034,385 | 7/1991 | DiNinno et al. | 540/302 |
| 5,037,820 | 8/1991 | DiNinno et al. | |

FOREIGN PATENT DOCUMENTS

| | | |
|---|---|---|
| 185315 | 6/1986 | European Pat. Off. |
| 0277743 | 8/1988 | European Pat. Off. |

OTHER PUBLICATIONS

Bryce et al. Bull. Soc. Chim. Fr. 1986 (6) 930-932.
L. D. Cama et al., Total Synthesis of Thienamycin Analogs-III Tetrahedron 39, 2531 (1983).
R. N. Guthikonda et al., Structure Activity Relationship in the 2-Arylcarbapenem Series, J. Med. Chem., 30, 871 (1987).

*Primary Examiner*—Marianne M. Cintins
*Assistant Examiner*—Rebecca Cook
*Attorney, Agent, or Firm*—Richard C. Billups; Joseph F. DiPrima

[57] ABSTRACT

Carbapenems of the formula

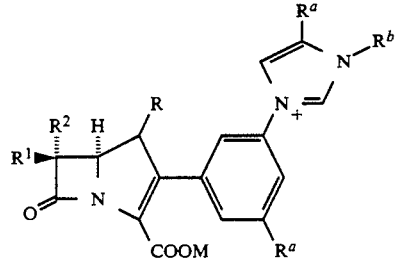

are useful antibacterial agents.

6 Claims, No Drawings

2-(N-IMIDAZOLIUMPHENYL)-CARBAPENEMS

BACKGROUND OF THE INVENTION

The present invention relates to antibacterial agents of the carbapenem class, in which the 2-position sidechain is characterized by a N-imidazoliumphenyl moiety, substituted by various neutral substituents, as described in more detail further below.

Thienamycin was an early carbapenem antibacterial agent having a broad spectrum; it has the following formula:

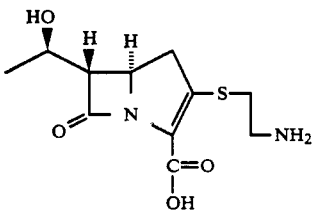

Later, N-formimidoyl thienamycin was discovered; it has the formula:

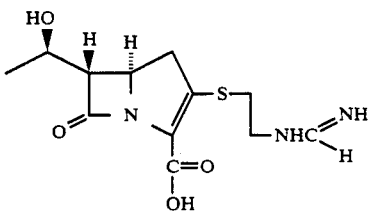

The 2-(N-imidazoliumphenyl)-carbapenems of the present invention are not only of interest for a broad antibacterial spectrum such as that of thienamycin or N-formimidoyl thienamycin. Rather, their spectrum of activity of special interest is to gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

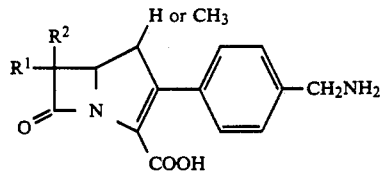

However, there is no description or suggestion of a N-imidazoliumphenyl 2-substituent such as characterizes the compounds of the present invention, nor is there any suggestion of the suprisingly better anti-MRSA/MRCNS activity of the compounds of the present invention.

U.S. Pat. No. 4,978,659 describes a particular class of compounds of the formula:

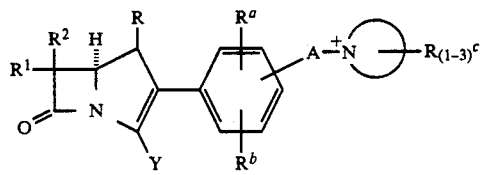

but this limited teaching in no way suggests the totally different compounds of the present invention, not their surprisingly better anti-MRSA/MRCNS activity.

SUMMARY OF INVENTION

The present invention provides novel carbapenem compounds of the formula:

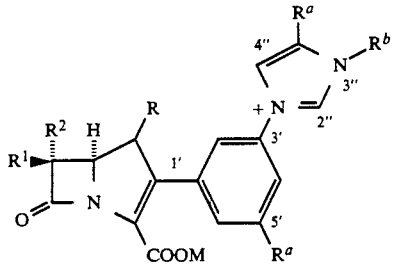

wherein:
R is H or $CH_3$;
$R^1$ and $R^2$ are independently H, $CH_3$—, $CH_3CH_2$—, $(CH_3)_2CH$—, $HOCH_2$—, $CH_3CH(OH)$—, $(CH_3)_2C(OH)$—, $FCH_2CH(OH)$—, $F_2CHCH(OH)$—, $F_3CCH(OH)$—, $CH_3CH(F)$—, $CH_3CF_2$—, or $(CH_3)_2C(F)$—;
$R^b$ is H, —$NH_2$, $C_1$-$C_4$alkyl, —($C_1$-$C_4$alkyl)—OH or (phenyl)$C_1$-$C_4$alkyl—;
$R^a$ are independently selected from the group consisting of hydrogen and the radicals set out below:
a) a trifluoromethyl group: —$CF_3$;
b) a halogen atom: —Br, —Cl, —F, or —I;
c) $C_1$-$C_4$ alkoxy radical: —$OC_{1-4}$ alkyl, wherein the alkyl is optionally mono-substituted by $R^q$, where $R^q$ is a member selected from the group consisting of —OH, —$OCH_3$, —CN, —C(O)$NH_2$, —OC(O)$NH_2$, CHO, —OC(O)N($CH_3$)$_2$, —$SO_2NH_2$, —$SO_2N(CH_3)_2$, —$SOCH_3$, —$SO_2CH_3$, —F, —$CF_3$, —COO$M^a$ (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and —$SO_3M^b$ (where $M^b$ is hydrogen or an alkali metal);

d) a hydroxy group; —OH;

e) a carbonyloxy radical: —O(C=O)$R^s$, where $R^s$ is $C_{1-4}$ alkyl or phenyl, each of which is optionally mono-substituted by $R^q$ as defined above or tri-substituted with —F;

f) a carbamoyloxy radical: —O(C=O)N($R^y$)$R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical interrupted by —O—, —S—, —S(O)— or —S(O)$_2$— to form a ring (where the ring is optionally mono-substituted with Rq as defined above);

g) a sulfur radical: —S(O)$_n$—$R^s$ where n=0-2, and $R^s$ is defined above;

h) a sulfamoyl group: —SO$_2$N($R^y$)$R^z$ where $R^y$ and $R^z$ are as defined above;

i) azido: $N_3$ j) a formamido group: —N($R^t$)(C=O)H, where $R^t$ is H or $C_{1-4}$ alkyl, and the alkyl thereof is optionally mono-substituted by $R^q$ as defined above;

k) a ($C_1$-$C_4$ alkyl)carbonylamino radical: —N($R^t$)(C=O)$C_{1-4}$ alkyl, where $R^t$ is as defined above, and the alkyl group is also optionally mono-substituted by $R^q$ as defined above;

l) a ($C_1$-$C_4$ alkoxy)carbonylamino radical: —N($R^t$)(C=O)O$C_{1-4}$ alkyl, where $R^t$ is as defined above, and the alkyl group is also optionally mono-substituted by $R^q$ as defined above;

m) a ureido group: —N($R^t$) (C=O)N($R^y$)$R^z$ where $R^t$, $R^y$ and $R^z$ are as defined above;

n) a sulfonamido group: —N($R^t$)SO$_2R^s$, where $R^s$ and $R^t$ are as defined above;

o) a cyano group: —CN;

p) a formyl or acetalized formyl radical: —(C=O)H or —CH(OCH$_3$)$_2$;

q) ($C_1$-$C_4$ alkyl)carbonyl radical wherein the carbonyl is acetalized: —C(OCH$_3$)$_2C_{1-4}$ alkyl, where the alkyl is optionally mono-substituted by $R^q$ as defined above;

r) carbonyl radical: —(C=O)$R^s$, where $R^s$ is as defined above;

s) a hydroximinomethyl radical in which the oxygen or carbon atom is optionally substituted by a $C_1$-$C_4$ alkyl group: —(C=NO$R^z$)$R^y$ where $R^y$ and $R^z$ are as defined above, except they may not be joined together to form a ring;

t) a ($C_1$-$C_4$ alkoxy)carbonyl radical: —(C=O)O$C_{1-4}$ alkyl, where the alkyl is optionally mono-substituted by $R^q$ as defined above;

u) a carbamoyl radical: —(C=O)N($R^y$)$R^z$ where $R^y$ and $R^z$ are as defined above;

v) an N-hydroxycarbamoyl or N($C_1$-$C_4$ alkoxy)carbamoyl radical in which the nitrogen atom may be additionally substituted by a $C_1$-$C_4$ alkyl group: —(C=O)—N(O$R^y$)$R^z$ where $R^y$ and $R^z$ are as defined above, except they may not be joined together to form a ring;

w) a thiocarbamoyl group: —(C=S)N($R^y$)($R^z$) where $R^y$ and $R^z$ are as defined above;

x) carboxyl: —COO$M^b$, where $M^b$ is as defined above;

y) thiocyanate: —SCN;

z) trifluoromethylthio: —SCF$_3$;

aa) tetrazolyl, where the point of attachment is the carbon atom of the tetrazole ring and one of the nitrogen atoms is mono-substituted by hydrogen, an alkali metal or a $C_1$-$C_4$ alkyl optionally substituted by $R^q$ as defined above;

ab) an anionic function selected from the group consisting of: phosphono [P=O(O$M^b$)$_2$]; alkylphosphono {P=O(O$M^b$)-[O($C_1$-$C_4$ alkyl)]}; alkylphosphinyl [P=O(O$M^b$)-($C_1$-$C_4$alkyl)]; phosphoramido [P=O(O$M^b$)N($R^y$)$R^z$ and P=O(O$M^b$)NH$R^x$]; sulfino (SO$_2M^b$); sulfo (SO$_3M^b$); acylsulfonamides selected from the structures CON$M^b$SO$_2R^x$, CON$M^b$SO$_2$N($R^y$)$R^z$, SO$_2$N$M^b$CON($R^y$)$R^z$; and SO$_2$N$M^b$CN, where $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;

ac) $C_5$-$C_7$ cycloalkyl group in which one of the carbon atoms in the ring is replaced by a heteroatom selected from O, S, NH or N($C_1$-$C_4$ alkyl) and in which one additional carbon atom may be replaced by NH or N($C_1$-$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2$-$C_4$ alkenyl radical, optionally mono-substituted by one of the substituents a) to ac) above and phenyl which is optionally substituted by $R^q$ as defined above;

ae) $C_2$-$C_4$ alkynyl radical, optionally mono-substituted by one of the substituents a) to ac) above;

af) $C_1$-$C_4$ alkyl radical;

ag) $C_1$-$C_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from —S— and N$R^t$ (where $R^t$ is as defined above) and one of the saturated carbon atoms of the oxazolidinone ring is optionally mono-substituted by one of the substituents a) to ag) above; and M is selected from:

i) hydrogen;

ii) a pharmaceutically acceptable esterifying group or removable carboxyl protecting group;

iii) an alkali metal or other pharmaceutically acceptable cation; or iv) absent, leaving COO−.

The present invention also provides novel carbapenem intermediates of the formula:

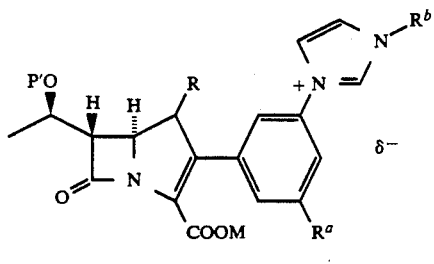

wherein:
R is H or CH$_3$;
R$^a$ is —SnMe$_3$;
R$^b$ is H, —NH$_2$, C$_1$-C$_4$alkyl, —(C$_{1-4}$alkyl)—OH or (phenyl)C$_1$-C$_4$alkyl—;
δ$^-$ is a counterion;
P' is H or a removable protecting group for hydroxy; and
M is a removable protecting group for carboxy.

DETAILED DESCRIPTION OF THE INVENTION

The manufacture of compounds of Formula I may be carried out in a three-stage synthesis scheme followed by a final step which allows for the removal of any protecting groups. The objective of a first synthetic stage is to produce a base N-imidazoliumphenyl compound which may be converted to the two-position substituent of the carbapenem of Formula I. The objective of a second synthetic stage is to attach the base N-imidazoliumphenyl to the carbapenem. Finally, the objective of a third synthetic stage is to introduce the desired R$^a$ and R$^b$. This third synthetic stage may be performed at any point according to the nature of the various R$^a$ and R$^b$.

Flow Sheets A and B demonstrate a suggested first stage synthesis. Flow Sheet C demonstrates a second stage synthesis in which the products of Flow Sheets A and B may be utilized. The third synthesis varies according to the selected R$^a$ and R$^b$.

The suggested first synthesis of Flow Sheet A can generally be outlined as a condensation between an amine and an isothiocyanate to form a thiourea followed by a cyclization to an imidazole. Referring to Flow Sheet A, 3-bromoaniline A1 is converted to the isothiocyanate A2 by reaction with CSCl$_2$. This reaction may be carried out in a two phase medium of water and dichloromethane, at 0° to 50° C. with calcium carbonate. The resultant compound A2 is reacted with an appropriate acetal to form thiourea A3. This is a simple condensation reaction which may be effected by heating the reactants under reflux conditions using inert solvents, e.g., ethanol, toluene or DMF at 80° C. A dimethylacetal is shown in Flow Sheet A although, clearly, a diethylacetal could also be used. The thiourea A3 is subjected to a cyclization reaction to form the imidazole A4 bearing a sulfhydryl substituent. The cyclization reaction may be carried out by treatment of A3 with acid, preferably by refluxing the intermediates with aqueous hydrochloric acid in ethanol. The sulfhydryl substituent of A4 is subsequently removed to produce imidazole A5. This removal might be by catalytic reduction (i.e. desulfurization) preferably utilizing Raney nickel or by oxidation with dilute nitric acid at 80° C. to 90° C. Imidazole A5 may be appropriately N-substituted, as such, to produce the N-imidazoliumphenyl A7 which is followed by substitution with a trimethylstannyl group to produce N-imidazoliumphenyl C1. Inversely, imidazole A5 may be first substituted with a trimethylstannyl moiety to directly produce N-imidazoliumphenyl C1 upon N-substitution.

The N-substitution of N-imidazoliumphenyl may be accomplished by reacting either imidazole A5 or A6 with an alkylating agent R$^b$—Y$^1$ to produce A7 or C1, respectively. Moiety R$^b$ is described above and stable to the conditions of the reaction or is a substituent described above and appropriately protected or is a stable precursor substituent to a substituent described above. The reaction is generally carried out in an inert organic solvent (e.g. CH$_2$Cl$_2$) at a temperature from −80° C. to room temperature. Y$^1$ is a leaving group, such as, iodide, bromide, mesylate (methanesulfonate), tosylate (p-toluenesulfonate) or O-triflate (trifluoromethanesulfonate). Alternatively, the N-substitution may be obtained by reaction with an amidinating agent, such as, o-(2,4,6-triisopropylbenzenesulfonyl)hydroxylamine, giving the N-amino derivative, in a suitable solvent (e.g. CH$_2$Cl$_2$ or CH$_3$CN) at about room temperature. Intermediate A6 may be obtained from A5 or C1 from A7 by reaction with hexamethylditin in the presence of a palladium(0) catalyst such as tetrakis(triphenylphosphine)-palladium(0) in an inert solvent such as toluene at from 25° C. to 110° C. for from 0.25-24 hours to provide the stannane.

The acetal for reaction with thiourea A2 is depicted as R$^a$ substituted. This R$^a$ is defined above and must, of course, be stable to the reactions to follow or it may be a protected form of R$^a$ or it may be a stable precursor to R$^a$. Suitable R$^a$ include C$_1$-C$_4$ alkyl, such as methyl, which might also serve as a precursor substituent, or protected hydroxymethyl.

FLOW SHEET A

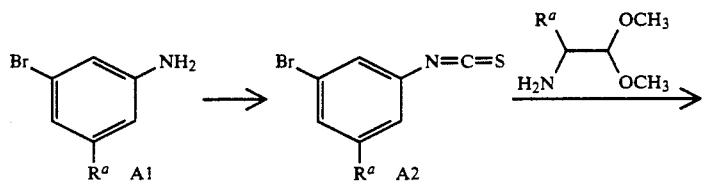

FLOW SHEET A

-continued

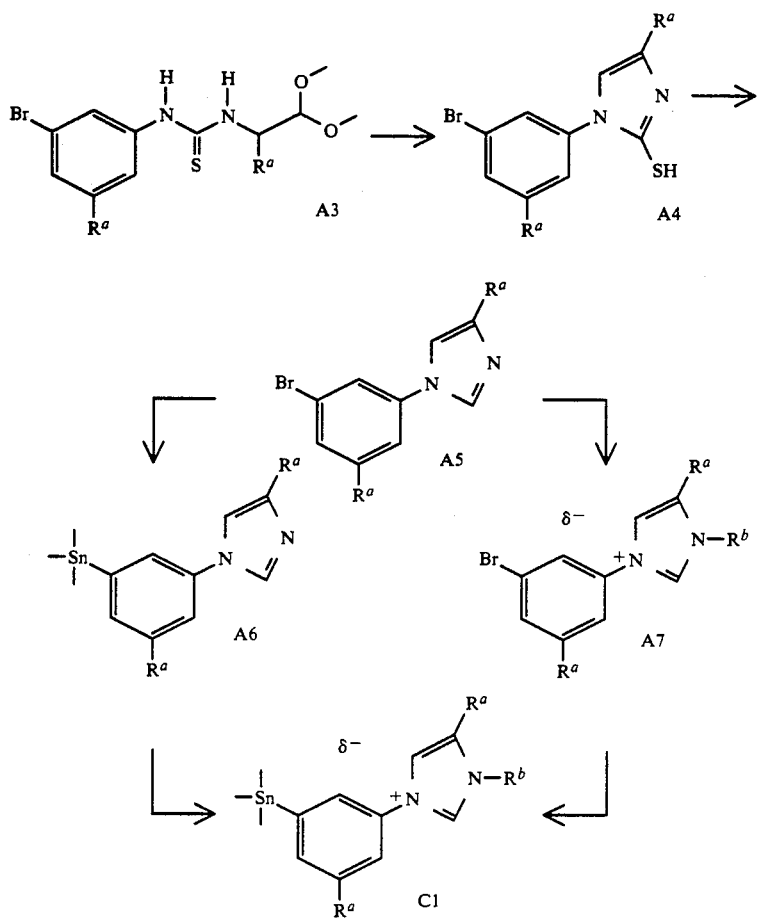

The suggested second synthesis of Flow Sheet B provides two alternative syntheses from A1 to A5 and thus eventually to C1. Referring to Flow Sheet B, 3-bromoaniline A1 is heated with an acid catalyst and an orthoformate of the type, $HC(OC_1-C_4alkyl)_3$ to produce imidate B1. Imidate B1 might be employed as a starting material for either of two routes to reach imidazole A5. In a first route, a formamidine B3 is produced by heating B1 with $NH_3$ in alcohol and dioxane. The formamidine is subsequently reacted with 1,1-dimethoxy-2-bromoethane by heating in an inert solvent, such as dioxane, to produce imidazole A5. In a second route, compound B2 is produced by heating B1 with 1,1-dimethoxy-2-aminoethane in an inert solvent, such as dioxane, or alcohol. Compound B2 might be ring closed to imidazole A5 by refluxing in alcohol with an acid catalyst. Imidazole A5 might be converted to stannane C1 as described in Flow Sheet A. In regard to the syntheses of Flow Sheet B, reference is made to Roger, et al., Chem. Rev., vol. 61, 179–211 (1961) and Bredereck, H., Chem. Br., vol. 97, 827–829 (1964).

In the art there are still further syntheses by which C1 might be produced. For example, further syntheses are suggested in "Comprehensive Heterocyclic Chemistry", Katritzky, A. R., Pergamon Press, N.Y., p. 457 etc., 1984. In one route suggested therein, intermediate A5 might be produced by heating appropriately substituted $\phi NHCH_2CH_2NH_2$ with an acid catalyst and an orthoformate of the type, $HC(OC_1-C_4alkyl)_3$ in an inert solvent to produce 2-imidazolin-1-yl-$\phi$. The 2-imidazolin-1-yl portion of this intermediate might be oxidized to an imidazole A5 equivalent using $MnO_2$ in an inert solvent. In a second but similar route, 2-imidazolin-1-yl-$\phi$ might be obtained by heating appropriately substituted $\phi NHCH_2CH_2NH_2$ in HCOOH and subsequently oxidized as described to an imidazole A5 equivalent. In a third route, an imidazole A5 equivalent might be produced in one step by reacting appropriately substituted formimine of the formula $\phi-N=CH_2$ with toluene-p-sulfonylisocyanide, p-methyl$\phi SO_2CH_2-C=N$. In each case, the A5 equivalent might be converted to C1 by methods described above.

FLOW SHEET B

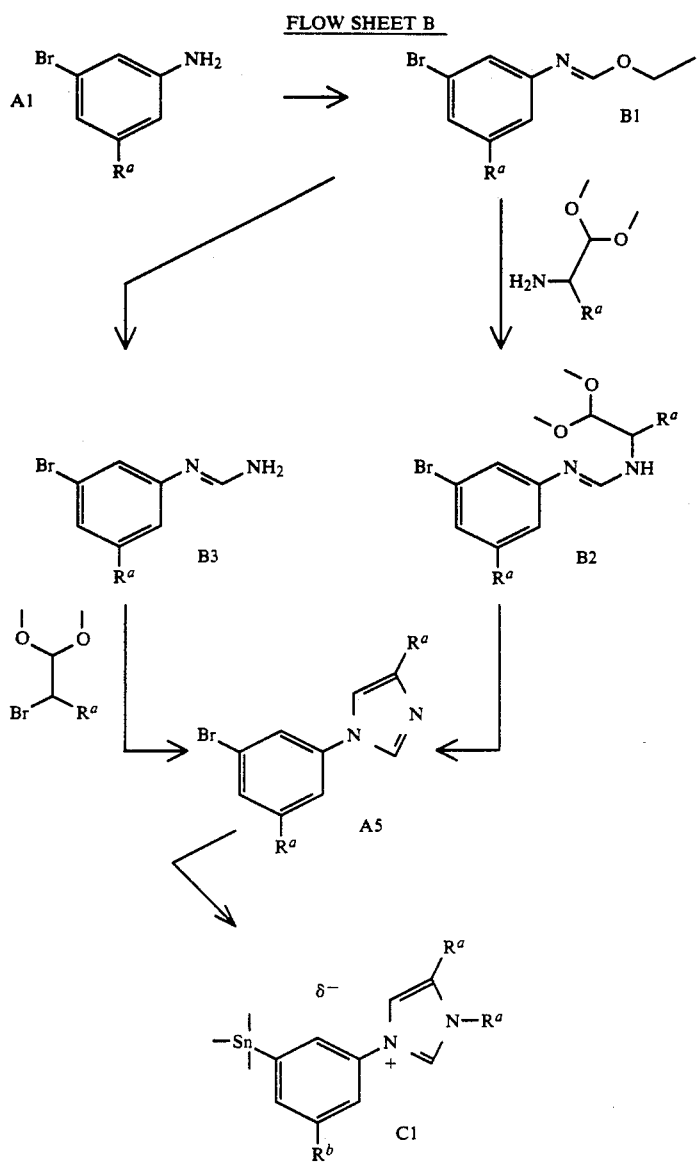

The object compound of Flows Sheets A and B form the nucleus of the 2-position substitution of the carbapenem compounds taught herein. As such it is shown to be $R^a$ and $R^b$ substituted. However, it is immediately clear to persons skilled in the art that certain $R^a$ and $R^b$ listed above, if substituted on intermediates to C1 would not survive or permit the synthesis to compound C1. Thus, where a certain $R^a$ or $R^b$ is desired and this $R^a$ or $R^b$ is not compatible with the synthesis scheme to produce C1 then a compatible precursor substituent might be employed through the synthesis.

The identity of the precursor substituent employed is not crucial so long as it does not interfere with the synthesis to C1 and so long as it might be thereafter converted to more desireable substituent. Preferred precursor substituents for $R^a$ are methyl, hydroxymethyl, protected hydroxymethyl, hydroxy propyl, protected hydroxy propyl and trimethylstannyl.

Thus, as to the $R^a$ or $R^b$ substituent on compound C1, it might be an $R^a$ or $R^b$ with or without protecting groups stable to the conditions of producing compound C1, and stable to the conditions of subsequently adding C1, to the carbapenem. Alternatively, it might be a stable precursor substituent which is stable to the conditions of making C1, which is optionally stable to the conditions of adding C1, to the carbapenem and which is convertible to a desired $R^a$ or $R^b$ or to another precursor substituent.

As stated above, a second stage synthesis is to attach the base N-imidazoliumphenyl, such as, C1 to the 2-position of the carbapenem. This synthesis involves a palladium catalyzed cross-coupling reaction between a carbapenem triflate and a suitably substituted arylstannane, a process which is described in U.S. patent application Ser. No. 650,011 filed Feb. 4, 1991, hereby incorporated by reference. Referring to Flow Sheet C, the 2-oxocarbapenam is reacted with a suitable trifluoromethanesulfonyl source, such as trifluoromethanesulfonic anhydride, in the presence of an organic nitrogen base, such as triethylamine, diisopropylamine, diisopropylethylamine and the like, in polar aprotic solvent, such as tetrahydrofuran or methylene chloride. Optionally, an organic nitrogen base, such as triethylamine and the like, is then added to the reaction solution followed immediately by a silylating agent, such as trialkylsilyl trifluoromethanesulfonate to provide intermediate C2. An aprotic polar coordinating solvent, such as DMF, 1-methyl-2-pyrrolidinone and the like, is optionally added. This is followed by the addition of a palladium compound, such as tris(dibenzylideneacetone)dipalladium-chloroform, palladium acetate and the like, and the stannane C1. A halide source, such as lithium chloride, zinc chloride or tetraalkylammonium chlorides and the like, is added and the reaction solution is allowed to warm and is stirred at a suitable temperature, such as 0° to 50° C. for from a few minutes to 48 hours. The carbapenem C4 is obtained by conventional isolation/purification methodology known in the art.

It is clear that in each instance where a charged N-imidazoliumphenyl is shown or discussed, there is by necessity a counterion $\delta^-$. Thus, intermediates A7, C1, C4 and the preferred intermediates described above, as well as the active compounds, have a counterion to the charged N-imidazoliumphenyl. The identity of the counterion will, initially at least, depend on the leaving group employed in the substitution of the imidazole. Herein, for example, $\delta^-$ might be the residue of iodide, mesylate, tosylate, etc. Of course, the counterion is easily replaced with various counterions which have no connection to the counterion formation. For example, chloride is not a highly reactive leaving group, but as $Cl^-$ it can readily serve as a suitable replacement counterion.

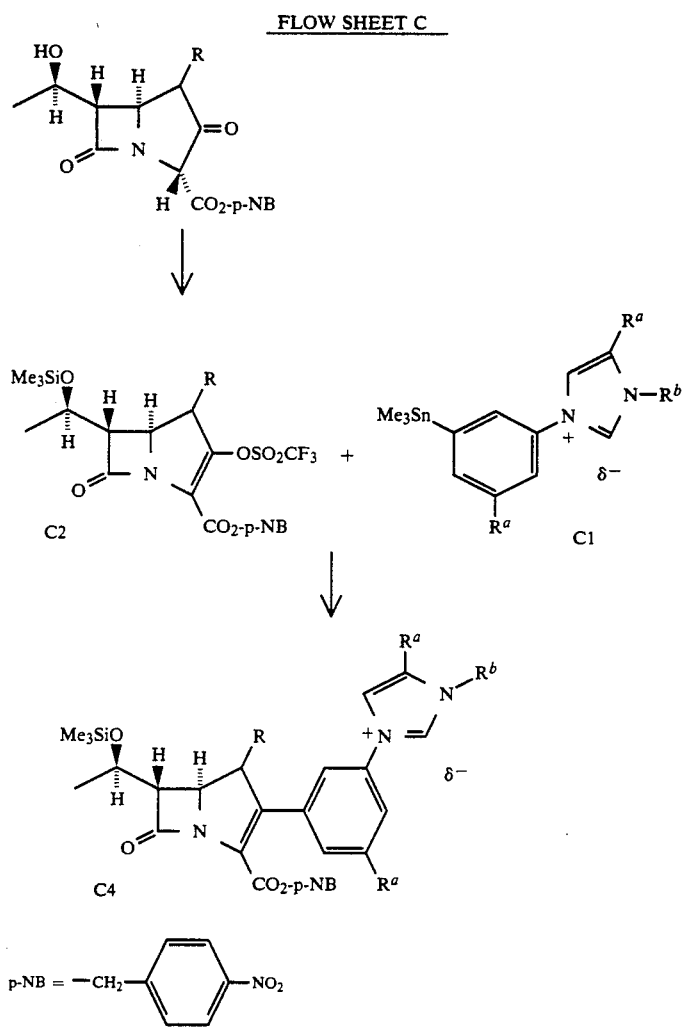

FLOW SHEET C

Generally speaking, the mild conditions of the synthesis shown in Flow Sheet C allow for a range of functional groups $R^a$ or $R^b$ to be present. However, in certain cases it is advantageous for the $R^a$ substituent(s) of the stannane C1 to be introduced in a protected or precursory form. Final elaboration of $R^a$ or $R^b$ from a precursor substituent, e.g. hydroxymethyl or hydroxypropyl, might be accomplished on carbapenem intermediate C4. Removal of hydroxyl and carboxyl protecting groups then provides the final compound of Formula I. Such final elaboration and deprotection is described in further detail below.

The steps for preparing the 2-oxocarbapenam intermediate of Flow Sheet C are well known in the art and are explained in ample detail by D. G. Melillo et al., Tetrahedron Letters, 1980, 21, 2783, T. Salzmann et al., J. Am. Chem. Soc., 1980, 102, 6161, and L. M. Fuentes, I. Shinkai, and T. N. Salzmann, J. Am. Chem. Soc., 1986, 108, 4675. The syntheses are also disclosed in U.S. Pat. No. 4,269,772, U.S. Pat. No. 4,350,631, U.S. Pat. No. 4,383,946 and U.S. Pat. No. 4,414,155 all assigned to Merck and Company, Inc. and hereby incorporated by reference.

The general synthesis description depicted above in the Flow Sheets shows a protected 1-hydroxyethyl substitution on the 6-position of the carbapenem. In certain situations, it might not be necessary to protect this substituent as shown. It might well be the case that an unprotected hydroxy substituent will survive the coupling of Flow Sheet C and subsequent manipulations of $R^a$ and $R^b$. Persons skilled in the art can determine those instances in which the protecting group is necessary.

After final deprotection, a 1-hydroxyethyl substituent is obtained, which is preferred in most cases. However, it has been found that with certain 2-side-chain selections, the ultimate balance of favorable properties in the overall molecule might be enhanced by selection of the 6-(1-fluoroethyl) moiety instead. Preparation of 6-fluoroalkyl compounds within the scope of the present invention is carried out in a straightforward manner, using techniques well known in the art of preparing carbapenem antibacterial compounds. See, e.g., J. G. deVries et al., *Heterocycles*, 1985, 23, 1915; BE 900 718 A (Sandoz) and Japanese Patent Pub. No. 6-0163-882-A (Sanruku Ocean).

In preferred compounds of Formula I, $R^1$ is hydrogen. More preferably, $R^1$ is hydrogen and $R^2$ is (R)—$CH_3CH(OH)$— or (R)—$CH_3CH(F)$—. In the most preferred case, $R^1$ is hydrogen and $R^2$ is (R)—$CH_3CH(OH)$—. While R=H is usually preferred, there are instances in which R=$CH_3$ might provide improved chemical stability, water solubility, or pharmacokinetic behavior. The substituent R=$CH_3$ may be of either configuration, i.e., the $\alpha$ or $\beta$-stereoisomer. Additionally, in preferred compounds, at least $R^a$ in the 5'-position of the N-imidazoliumphenyl is other than hydrogen. In the most preferred compounds, $R^a$ in the 4''-position is hydrogen.

Suitable $R^a$ are described above in the text associated with Formula I. Among preferred $R^a$ are $C_{1-4}$ alkyl mono-substituted with hydroxy, such as, hydroxymethyl; formyl; alkoxycarbonyl, such as, —$COOCH_3$; carbamoyl, such as, —$CONH_2$; hydroxoximinomethyl, such as, —CH=NOH; or cyano.

In regard to this preferred substitution, a hydroxymethyl might be obtained on either position for $R^a$ as follows. As one method, hydroxymethyl might be substituted on any of rings A1 or A2 or the acetal of Flow Sheet A by standard procedures and appropriately protected.

The preferred formyl substitution on the N-imidazoliumphenyl might be obtained on C4 from the hydroxymethyl substitution, in the case of $R^a$, by a Swern oxidation. For example, C4 is oxidized in methylene chloride at from −70° C. to room temperature employing oxalyl chloride-dimethyl sulfoxide followed by triethylamine as the active agent. Obviously, the position of the resultant formyl substitution will depend upon the position of the hydroxymethyl substitution on C4.

The preferred —CH=NOH substitution on the N-imidazoliumphenyl might be conveniently obtained from the formyl substitution just described. This is accomplished simply by exposing the formyl substituted compound to hydroxylamine in an appropriate solvent at room temperature.

The preferred cyano substitution on the N-imidazoliumphenyl might be obtained from a substituted A5 or A7, for example, in which $R^a$ is bromine. The bromine substituted compound is reacted with copper (I) cyanide in N-methylpyrrolid-2-one (3 hours at 180° C.).

The preferred —$COOCH_3$ substitution on the N-imidazoliumphenyl might be obtained from a methyl substituted C1 or C4. The methyl substituent might be oxidized with chromium trioxide or $^nBu_4NMnO_4$ to form carboxy.

The preferred carbamoyl substitution on the N-imidazoliumphenyl, might be obtained from C4 with carboxylic acid substitution as described immediately above. This carboxylic acid substituent is converted to the carboxamide group, —$CONH_2$, by sequentially contacting with 1-ethyl-3-(3-dimethylaminopropyl)carbodiimide hydrochloride, 1-hydroxybenzotriazole, and ammonia in an organic solvent at room temperature. Substituted amides might of course be obtained by replacing ammonia with the corresponding substituted amine. Alternatively, the carbamoyl substitution might be obtained by hydrolysis of the nitrile of the cyano substituent described above.

In the preparation methods described above, the carboxyl group at the 3-position and, optionally, the hydroxyl group at the 8-position of the carbapenem remain blocked by protecting groups until the penultimate product is prepared. Suitable hydroxyl protecting groups, P', are silyl groups such as trialkylsilyl, aryl(alkyl)alkoxysilyl, alkoxydiarylsilyl and diarylalkylsilyl and carbonate groups such as alkyloxycarbonyl, substituted alkyloxycarbonyl, benzyloxycarbonyl, substituted benzyloxycarbonyl, allyloxycarbonyl and substituted allyloxycarbonyl. The preferred protecting groups, in addition to or including those shown in the schemes, are t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Suitable carboxyl protecting groups, M, in addition to or including those shown in the schemes are described herein below.

Deblocking may be carried out in a conventional manner. Compound C4, if protected at the 8-position, is exposed initially to aqueous acidic conditions, acetic acid or dilute HCl or the like, in an organic solvent such as tetrahydrofuran at 0° C. to ambient temperature for from a few minutes to several hours. The resulting desilylated carbapenem may be isolated by conventional techniques, but is more conveniently taken into the final deprotection process. Thus, addition of an inorganic base such as $NaHCO_3$ or $KHCO_3$ and a catalyst, such as, 10% Pd/C or 5% $Rh/Al_2O_3$ followed by hydrogenation provides for the removal of the p-nitrobenzyl protecting group and the formation of the final compound of Formula I.

With reference to the above definitions, "alkyl" means a straight or branched chain aliphatic hydrocarbon radical.

The term "heteroatom" means N, S, or O, selected on an independent basis.

The term "heteroaryl" has been defined herein, in relation to the $R^x$ group, to have a specific and limited meaning, being only monocyclic. It is required that the monocyclic heteroaryl have at least one nitrogen atom, and optionally at most only one additional oxygen or sulfur heteroatom may be present. Heteroaryls of this type are pyrrole and pyridine (1N); and oxazole, thiazole or oxazine (1N + 1O or 1S). While additional nitrogen atoms may be present together with the first nitrogen and oxygen or sulfur, giving, e.g., a thiadiazole (2N's + 1S), the preferred heteroaryls are those where only nitrogen heteroatoms are present when there is more than one. Typical of these are pyrazole, imidazole, pyrimidine and pyrazine (2N's) and triazine (3N's).

The heteroaryl group of $R^x$ is always optionally mono-substituted by $R^q$, defined above, and substitution can be on one of the carbon atoms or one of the heteroatoms, although in the latter case certain substitutent choices may not be appropriate.

Listed in Tables I and II are specific compounds of the instant invention:

TABLE I

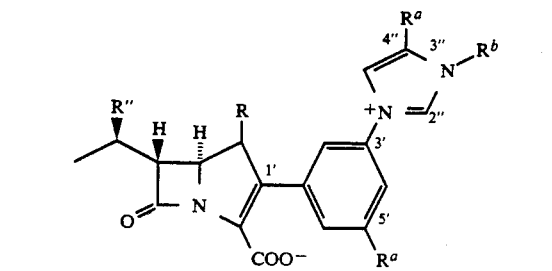

wherein R" is F or OH, R is H or Me and $R^a$ and $R^b$ are:

| # | $R^b$ | $R^a$ | $R^a$ position |
|---|---|---|---|
| 1 | —CH₃ | —H | — |
| 2 | —CH₃ | —OCH₃ | 5' |
| 3 | —CH₃ | —OCH₂CO₂CH₃ | 5' |
| 4 | —CH₃ | —OCH₂CH₂OH | 5' |
| 5 | —CH₃ | —CF₃ | 5' |
| 6 | —CH₃ | —F | 5' |
| 7 | —CH₃ | —Cl | 5' |
| 8 | —CH₃ | —Br | 5' |
| 9 | —NH₂ | —Br | 5' |
| 10 | —(CH₂)₃OH | —Br | 5' |
| 11 | —CH₃ | —I | 5' |
| 12 | —CH₃ | —OH | 5' |
| 13 | —CH₃ | —OCOCH₃ | 5' |
| 14 | —CH₃ | —OCONH₂ | 5' |
| 15 | —CH₃ | —SCH₃ | 5' |
| 16 | —CH₃ | —SOCH₃ | 5' |
| 17 | —CH₃ | —SO₂CH₃ | 5' |
| 18 | —CH₃ | —SCH₂CH₂OH | 5' |
| 19 | —CH₃ | —SOCH₂CH₂OH | 5' |
| 20 | —CH₃ | —SCH₂CONH₂ | 5' |
| 21 | —CH₃ | —SO₂NH₂ | 5' |
| 22 | —CH₃ | —SO₂N(CH₃)₂ | 5' |
| 23 | —CH₃ | —NHCHO | 5' |
| 24 | —CH₃ | —NHCOCH₃ | 5' |
| 25 | —CH₃ | —NHCO₂CH₃ | 5' |
| 26 | —CH₃ | —NHSO₂CH₃ | 5' |
| 27 | —CH₃ | —CN | 5' |
| 28 | —CH₃ | —CHO | 5' |
| 29 | —CH₃ | —COCH₃ | 5' |
| 30 | —CH₃ | —COCH₂OH | 5' |
| 31 | —CH₃ | —CH=NOH | 5' |
| 32 | —CH₃ | —CH=NOCH₃ | 5' |
| 33 | —CH₃ | —CH=NOCH₂CO₂CH₃ | 5' |
| 34 | —CH₃ | —CH=NOCMe₂CO₂CH₃ | 5' |
| 35 | —CH₃ | —CH=NOCMe₂CONH₂ | 5' |
| 36 | —CH₃ | —CO₂CH₂CH₂OH | 5' |
| 37 | —CH₃ | —CONH₂ | 5' |
| 38 | —CH₃ | —CONHCH₃ | 5' |
| 39 | —CH₃ | —CON(CH₃)₂ | 5' |
| 40 | —CH₃ | —CONHCH₂CN | 5' |
| 41 | —CH₃ | —CONHCH₂CONH₂ | 5' |
| 42 | —CH₃ | —CONHCH₂CO₂CH₃ | 5' |
| 43 | —CH₃ | —CONHOH | 5' |
| 44 | —CH₃ | —CONHOCH₃ | 5' |
| 45 | —CH₃ | -tetrazolyl | 5' |
| 46 | —CH₃ | —CO₂CH₃ | 5' |
| 47 | —CH₃ | —SCF₃ | 5' |
| 48 | —CH₃ | —CONHSO₂Ph | 5' |
| 49 | —CH₃ | —CONHSO₂NH₂ | 5' |
| 50 | —CH₃ | —SO₂CF₃ | 5' |
| 51 | —CH₃ | —SO₂NHCN | 5' |

TABLE I-continued

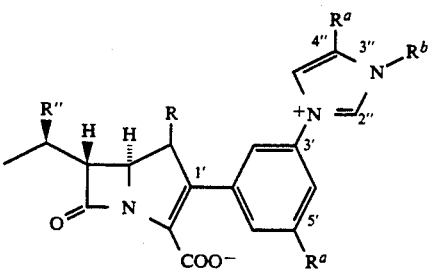

wherein R" is F or OH, R is H or Me and $R^a$ and $R^b$ are:

| # | $R^b$ | $R^a$ | $R^a$ position |
|---|---|---|---|
| 52 | —CH₃ | —SO₂NHCONH₂ | 5' |
| 53 | —CH₃ | —CH=CHCN | 5' |
| 54 | —CH₃ | —CH=CHCONH₂ | 5' |
| 55 | —CH₃ | —CH=CHCO₂CH₃ | 5' |
| 56 | —CH₃ | —C≡C—CONH₂ | 5' |
| 57 | —CH₃ | —C≡C—CN | 5' |
| 58 | —CH₃ | —CH₂OH | 5' |
| 59 | —CH₃ | —CH₂CO₂CH₃ | 5' |
| 60 | —CH₃ | —SO₂CH₂CH₂OH | 5' |
| 61 | —CH₃ | —CH₂I | 5' |
| 62 | —CH₂phenyl | —CONH₂ | 5' |
| 63 | —NH₂ | —CONH₂ | 5' |
| 64 | —CH₃ | —CONH₂ | 5', 4" |
| 65 | —CH₂phenyl | —CN | 5' |
| 66 | —NH₂ | —CN | 5' |
| 67 | —CH₃ | —CN | 5', 4" |
| 68 | —CH₂phenyl | —CHO | 5' |
| 69 | —NH₂ | —CHO | 5' |
| 70 | —CH₃ | —CHO | 5', 4" |
| 71 | —CH₂phenyl | —CH₂OH | 5' |
| 72 | —NH₂ | —CH₂OH | 5' |
| 73 | —CH₃ | —CH₂OH | 5', 4" |
| 74 | —CH₂phenyl | —S(O)CH₃ | 5' |
| 75 | —NH₂ | —S(O)CH₃ | 5' |
| 76 | —CH₃ | —S(O)CH₃ | 5', 4" |
| 77 | —CH₂phenyl | —SO₂CH₃ | 5' |
| 78 | —NH₂ | —SO₂CH₃ | 5' |
| 79 | —CH₃ | —SO₂CH₃ | 5', 4" |
| 80 | —CH₂phenyl | —I | 5' |
| 81 | —NH₂ | —I | 5' |
| 82 | —CH₃ | —I | 5' |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Broadly, such ester protecting groups include alkyl, substituted alkyl, benzyl, substituted benzyl, aryl, substituted aryl, allyl, substituted allyl and triorganosilyl. Examples of specific such ester protecting groups include benzhydryl, p-nitrobenzyl, 2-naphthylmethyl, allyl, 2-chloroallyl, benzyl, t-butyl, 2,2,2-trichloroethyl, t-butyldimethylsilyl, t-butyldiphenylsilyl, trimethylsilyl, 2-(trimethyl)silylethyl, phenacyl, p-methoxybenzyl, acetonyl, o-nitrobenzyl and 4-pyridylmethyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5-50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5-25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

EXAMPLE 1

(3,5-Dibromophenyl)isothiocyanate. 1

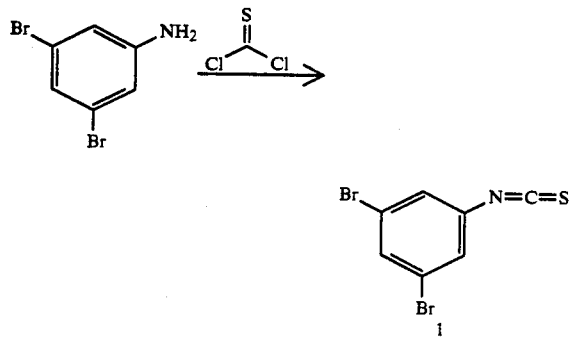

Commercially available 3,5-dibromoaniline (10 gm, 0.04 mol) was dissolved in $CH_2Cl_2$ (10 ml). The solution was added to a mixture of water (50 ml), $CH_2Cl_2$ (30 ml), thiophosgene (3.5 ml, 0.046 mol) and finely powdered $CaCO_3$ (5.99 g, 0.06 mol) with ice bath cooling. The mixture was allowed to come to RT, and stirred 16 Hrs. The mixture was heated briefly to 40° C., cooled to RT and filtered. The aqueous phase was extracted with $CH_2Cl_2$, and the combined organic phases washed with 0.2N HCl, $H_2O$ and brine. The organic extracts were dried with $MgSO_4$, filtered and reduced i. vac. The product was recrystallized at low temperature from ether. The compound can also be purified by chromatography on $SiO_2$ with 2% ethyl acetate in hexane as eluent. The compound should not be recrystallized from ethanol as per literature references due to extensive solvolysis for the dihalo derivatives.

$^1$H NMR [300 MHz, $CDCl_3$] 7.56 (t, 1H, 1.7 Hz), 7.30 (d, 2H, 1.7 Hz).

IR ($CHCl_3$ solution) 2080 cm$^{-1}$ brd, 1573, 1552, 1420.

N-(3,5-dibromophenyl)-N'-(2,2-dimethoxyethyl)thiourea. 2

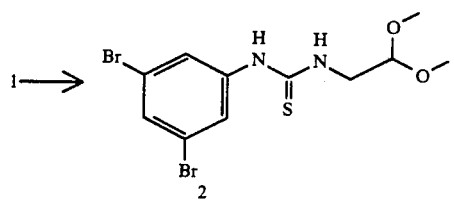

2,2-Dimethoxyethylamine (1.86 ml, 1.79 g, 0.017 mol) was dissolved in absolute ethanol (50 ml). Crystalline (3,5-dibromophenyl)isothiocyanate (5 g, 0.017 mol) was added, and the mixture heated to reflux. When TLC (1:1 Hexanes ethyl acetate, $SiO_2$) indicates consumption of starting material (~1 Hr), the mixture is allowed to cool to RT. The product crystallizes from the reaction mixture. Washing with abs. ethanol yields 4.5 g 2 (66%) as felted needles. Usual first crop recovery was 66–76%; several crops were taken. Total yield >90%.

$^1$H NMR [400 MHz, $CDCl_3$] 8.9 (brd, 1H), 7.50 (s, 1H), 7.40 (m, 2H), 6.5 (brd, 1H), 4.50 (t, 1H, 4.8 Hz), 3.78 (brd, 2H), 3.43 (s, 6H).

IR [$CHCl_3$] 3400 cm$^{-1}$, 2979, 2840, 1636, 1581, 1560, 1530, 1495, 1431, 1128, 1080.

1-(3',5'-dibromophenyl)imidazole. 4

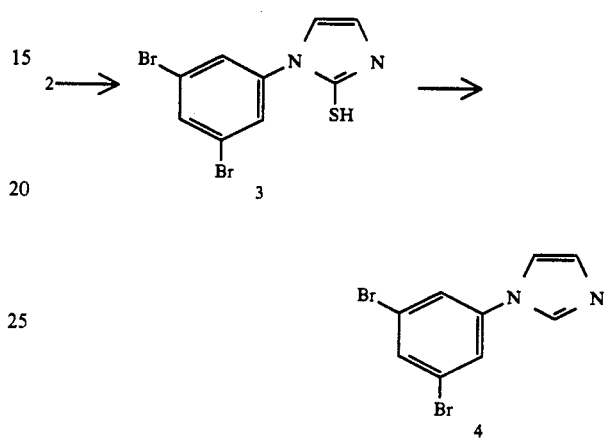

The thiourea 2 (4.5 g, 0.011 mol) was suspended in 9:1 10% aq HCl:ethanol, and the mixture heated to reflux. The starting material dissolves shortly before the product begins to crystallize from the reaction mixture. After TLC indicates complete consumption of SM (~1½ Hr) the mixture was cooled to RT, pH adjusted to ~6.5 with 10% KOH aq, and filtered. No attempt was made to purify the insoluble mercaptoimidazole 3.

$^1$H NMR [400 MHz, d6 Acetone] 8.02 (d, 2H, 1.7 Hz), 7.79 (t, 1H, 1.8 Hz), 7.33 (d, 1H, 2.6 Hz), 7.09 (d, 1H, 2.6 Hz), 2.9 exchangable H's.

IR [$CHCl_3$] 3695cm$^{-1}$, 3450, 1603, 1589, 1561, 1461, 1442, 1425, 1309.

The crude product 3 (2 g, 5.99 mmol) was covered with 20% $HNO_3$ (10 ml of a 29-100 dilution of concentrated $HNO_3$) in a 125 ml erlenmeyer. Very gentle heating initiates a vigorous evolution of gas. After spontaneous evolution of gas subsided, the mixture was heated to 100° C. for 10–15 min. The reaction was cooled and made strongly basic with 4N KOH aq. The aqueous phase was extracted with $CH_2Cl_2$, and the combined organic phases washed with $H_2O$ and brine. The organic phase was dried with $Na_2SO_4$, filtered and reduced i. vac. The crude solid 4 was purified by chromatography on $SiO_2$ (100 g) with 85:15 $CH_2Cl_2$ ethyl acetate as eluent. 1.5 g (83%) of white crystalline solid was obtained. The reaction was run on scales up to 32 g without problems.

$^1$H NMR [400 MHz, d6 Acetone] 8.23 (s, 1H), 7.9 (d, 2H, 1.67 Hz), 7.74 (t, 1H, 1.63 Hz), 7.72 (s,1H), 7.12 (s, 1H).

1-[5'-Bromo-3'-(trimethylstannyl)phenyl]imidazole 5 and 1-[3',5'-bis(trimethylstannyl)phenyl]imidazole. 6

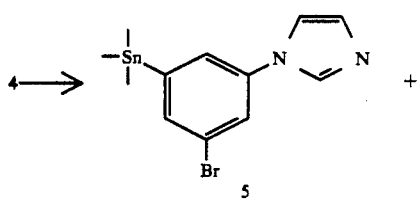

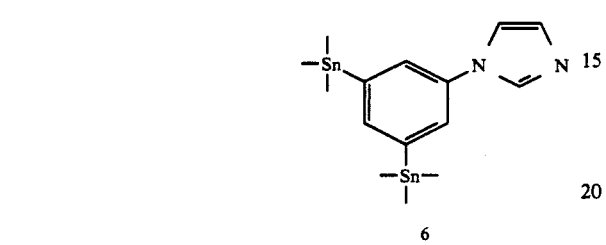

The dibromide 4 (9.6 g, 0.0317 mol) was dissolved in toluene (300 ml) with (Ph₃P)₄Pd (3.7 g, 0.0032 mol) and (Ph₃)P (831 mg, 0.0032 mol). Hexamethylditin (6.7 ml, 10.4 g, 0.0317 mol) was added, and the mixture degassed i. vac., and purged with N₂. The mixture was brought to reflux, and monitored by TLC for consumption of the dibromide. When SM was consumed (∼1½ HR) the reaction mixture was cooled and poured into CH₂Cl₂ and sat'd. NH₄Cl aq. The aqueous phase was extracted with CH₂Cl₂ three times, and the combined organic phases washed two more times with NH₄Cl aq. The organic phases were dried over Na₂SO₄, filtered and reduced i. vac. The crude solid was purified on SiO₂ (300 g) with 85:15 CCl₄ ethyl acetate as eluent. The yield of mono stannane 5 is ∼65%, plus ∼10% of the bis stannane 6. An approximately equal weight yield of the mono and bis products is obtained from 1.2 eq of hexamethylditin.

Mono-trimethylstannane 5

$^1$H NMR [400 MHz, CDCl₃] 7.82 (s, 1H), 7.56 (m, 1H), 7.46 (m, 1H), 7.37 (m, 1H), 7.24 (m, 1H, overlap CHCl₃), 7.19 (s, 1H), 0.34 (m, 9H).

Bis-trimethylstannane 6

$^1$H NMR [400 MHz, CDCl₃] 7.82 (s, 1H), 7.54 (m, 1H), 7.39 (m, 2H), 7.27 (s brd, 1H), 7.20 (s, 1H), 0.32 (m, 18H).

1-[5'-Bromo-3'-(trimethylstannyl)phenyl]-3-methylimidazolium triflate. 7

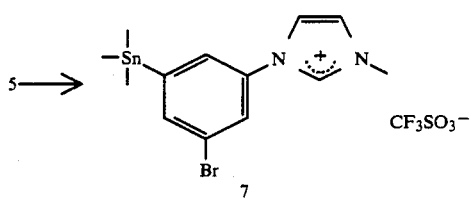

The imidazole 5 was dissolved in dry CH₂Cl₂ and cooled to −78° C. Neat methyl trifluoromethanesulfonate (0.95 ml, 1.38 g, 8.4 mmol) was added, and the solution allowed to warm to RT. The CH₂Cl₂ solution was washed with H₂O and dried over Na₂SO₄, filtered and reduced i. vac. The crystalline residue was recrystallized from toluene, containing ∼5% acetone. Recovery was typically >85% from two crops.

$^1$H NMR [CDCl₃, 300 MHz] 9.52 (s, 1H), 7.73 (m, 1H), 7.66 (m, 1H), 7.60 (m, 1H), 7.52 (m, 2H), 4.12 (s, 3H), 0.36 (m, 9H).

p-Nitrobenzyl (5R,6S)-2-[3'-bromo-5'[3''-methyl-1''-imidazolium]-phenyl]-6-[(1R)-1-hydroxyethyl]carbapen-2-em-3-carboxylate triflate. 9

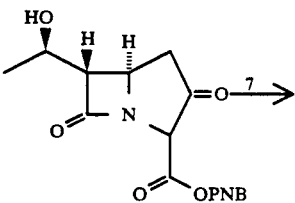

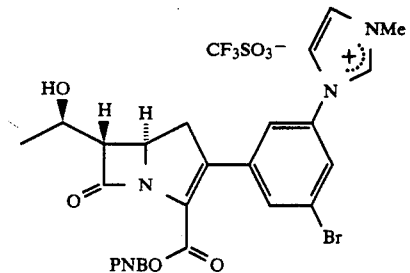

The bicyclic β-lactam (606 mg, 1.74 mmol) was dissolved in dry CH₂Cl₂ (10 ml) and cooled to −78° C. Diisopropylamine (0.27 ml, 1.92 mmol) was added, and the solution stirred 5 min. Neat trifluoromethanesulfonic anhydride (0.32 ml, 1.92 mmol) was added dropwise, and the resulting solution stirred 45 min at −78° C. to give a colorless suspension. Conversion to the enol triflate is monitored on E. Merck RP-18 analytical TLC plates with 98:2 toluene acetic acid as eluent. The stannane 7 (957 mg, 1.74 mmol) was dissolved in dry CH₂Cl₂ (5 ml, rinsed 5 ml) and added to the reaction mixture, followed by solid Pd₂DBA₃—CHCl₃ (181 mg, 0.174 mmol) and solid Et₄NCl-(H₂O)ₓ (289 mg, 1.74 mmol, figured on 166 g/mol). The reaction mixture was warmed immediately to RT in a water bath. The solution was stirred at RT until the enol triflate was consumed (TLC 70:30 ethyl acetate on SiO₂, or system indicated above). The reaction was worked up by pouring into a mixture of brine and H₂O (1:1), and CH₂Cl₂ and acetonitrile (1:1). The aqueous fraction was extracted several times with CH₂Cl₂/acetonitrile. The organic extracts were dried over Na₂SO₄, filtered and reduced i. vac. The usual recovery of the desired product was ∼60%. A yield is reported below over two steps. The product was usually deprotected without purification, but can be purified by chromatography on an E. Merck RP-18 Lobar column with acetone H₂O (72:28).

$^1$H NMR [400 MHz, d6 Acetone] 9.65 (s, 1H), 8.23 (t, 1H, 1.9 Hz), 8.19 (d, 2H, 8.8 Hz), 8.00 (t, 1H, 1.9 Hz), 7.98 (m, 2H), 7.88 (t, 1H, 1.5 Hz), 7.65 (d, 2H, 8.9 Hz), 5.35 (ABq, 2H, Δν59.4 Hz, J$_{AB}$ 13.8 Hz), 4.40 (m,1H), 4.19 (s, 1H), 4.19 (m, 1H), 3.49 (AB of ABX system, 2H, Δν113.5 Hz, J$_{AB}$ 18.6 Hz, J$_{AX}$ 10.3 Hz, J$_{BX}$ 8.5 Hz), 3.46 (dd, 1H, 3.1 , 6.2 Hz), 1.27 (d, 3H, 6.3 Hz).

(5R,6S)-2-[3'-bromo-5'[3"-methyl-1"-imidazolium]-phenyl]-6-[(1R)-1-hydroxyethyl]carbapen-2-em-3-carboxylate. 10

9⟶

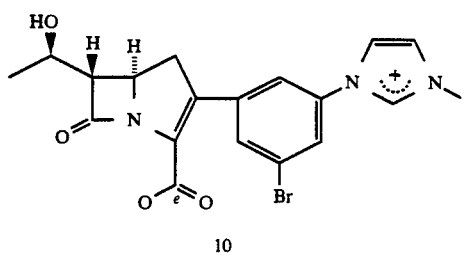

10

The p-nitrobenzyl ester 9 (116 mg, 0.17 mmol) was dissolved in 1:1 THF and ethanol (3 ml each). Sodium bicarbonate (21.5 mg, 0.25 mmol) was added in $H_2O$ (3 ml), followed by 5% Rh on $Al_2O_3$ (17.5 mg, 15 wt %). The reaction vessel was vacuum purged with $H_2$ three times and left to stir at RT. The consumption of the starting ester was monitored by TLC. Upon complete consumption of the ester, the mixture was filtered through a 0.45 m acrodisc, reduced i. vac. and residual water removed by lyophilization. The product was purified on an E. Merck RP-18 Lobar A column eluting with 85:15 water:acetonitrile. After lyophilization, 30.5 mg of carbapenem 10 was obtained. The typical yield was 30% over two steps. Compounds were characterized by $^1H$ NMR and UV.

$^1H$ NMR [400 MHz, $D_2O$, 15% $CD_3CN$] 9.39 (s, 1H, exchangable imidazolium CH), 8.02 (s, 1H), 7.94 (s, 1H), 7.89 (s, 1H), 7.80 (d, 1H, 1.8 Hz), 7.77 (s, 1H), 4.45 (m, 2H), 4.17 (s, 3H), 3.69 (dd, 1H, 2.7,5.5 Hz), 3.45 (AB of ABX system, 2H, $\Delta\nu$90.1 Hz, $J_{AB}$ 16.9 Hz, $J_{AX}$ 9.6 Hz, $J_{BX}$ 8.5 Hz), 1.47 (d, 3H).

UV [$H_2O$, 0.1M MOPS pH=7] $\lambda_{max}$=306nm, $\epsilon$=12047, C=~$7.10^{-5}$.

EXAMPLE 2

(3-Bromophenyl)isothiocyanate 11.

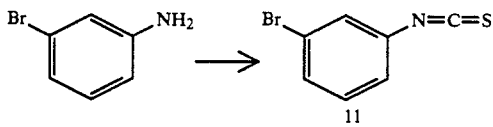

The isothiocyanate 11 was prepared as for compound 1. Five grams of m-bromoaniline yields 6.08 g of the isothiocyanate 11, purified by distillation (74° C. 1 mm).

N-(3-bromophenyl)-N'-(2,2-dimethoxyethyl)thiourea.12

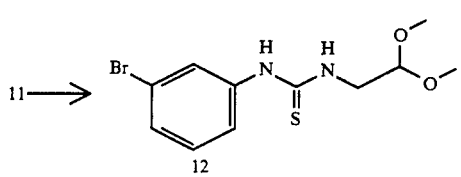

The thiourea 12 was prepared as for compound 2. 6.8 g of the isothiocyanate 11 leads to an essentially quantitative yield of the thiourea 12, purified as for 2.

$^1H$ NMR [200 MHz, $CDCl_3$]8.33 (brd, 1H), 7.43 (m, 2H), 7.29 (t, 1H, 4 Hz), 7.2 (m, 1H), 6.38 (brd, 1H), 4.54 (t, 1H, 2.8 Hz), 3.79 (m, 2H), 3.44 (s, 6H).

IR [$CHCl_3$] 3401 $cm^{-1}$, 2970, 2841, 1590, 1529, 1491, 1475, 1295, 1218, 1122, 1074.

1-(3'-bromophenyl)imidazole.14

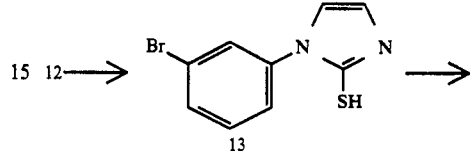

The imidazole 14 was prepared as for the imidazole 4. The yields of the imidazole 14 over two steps is 65%.

13 2-mercapto-1-(3'-bromophenyl)imidazole $^1H$ NMR [200 MHz, $CDCl_3$] 7.79 (t, 1H, 2 Hz), 7.6 (m, 2H), 7.39 (t, 1H, 8 Hz), 6.86 (d, 2H, 3.9 Hz).

IR [$CHCl_3$] 3455 $cm^{-1}$, 3145, 3097, 2978, 1591, 1483, 1448, 1431, 1317, 1290, 1251, 1148, 1095, 1070, 918.

14 1-(3'-bromophenyl)imidazole $^1H$ NMR [200 MHz, $CDCl_3$] 7.85 (s, 1H), 7.59 (m, 1H), 7.53 (m, 1H), 7.36 (m, 2H), 7.27 (m, 1H), 7.22 (d, 1H, ~1 Hz).

1-[3'-(trimethylstannyl)phenyl]imidazole 15

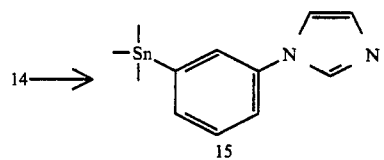

The stannane 15 was prepared as for compound 5. 500 mg of bromide 14 yields 450 mg stannane 15, 65%.

$^1H$ NMR [200 MHz, $CDCl_3$] 7.82 (s, 1H), 7.46 (m, 3H), 7.30 (m, 1H), 7.26 (m, 1H), 7.19 (s, 1H), 0.32 (m, 9H).

1-[3'-(trimethylstannyl)phenyl]-3-methylimidazolium triflate.16

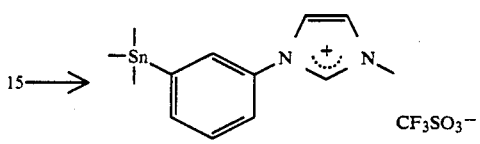

The imidazolium salt 16 was prepared as for compound 7. The yield is essentially quantitative.

¹H NMR [200 MHz, CDCl₃] 9.45 (s, 1H), 7.55 (m, 4H), 7.45 (m, 2H), 4.12 (s, 3H), 0.36 (m, 9H).

p-Nitrobenzyl (5R,6S)-2-[3'-[3''-methyl-1''-imidazolium]phenyl]-6-[(1R)-1-hydroxyethyl]carbapen-2-em-3-carboxylate trifluoromethanesulfonate. 17

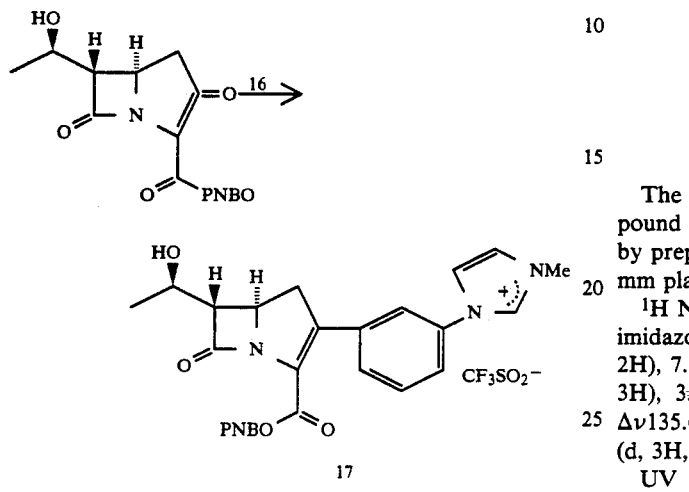

The bicyclic β-lactam (71 mg, 0.204 mmol) was dissolved in dry CH₂Cl₂ (1.5 ml) and cooled to −78° C. Diisopropylamine (31.5 ml, 0.224 mmol) was added, and the solution stirred 5 min. Neat trifluoromethanesulfonic anhydride (38 ml, 0.224 mmol) was added dropwise, and the resulting solution stirred 45 min at −78° C. to give a colorless suspension. Conversion to the enol triflate is monitored on E. Merck RP-18 analytical TLC plates with 98:2 toluene acetic acid as eluent. The stannane 16 (96 mg, 0.204 mmol) was dissolved in dry N-methyl-2-pyrrolidinone (1 ml, rinsed 0.5 ml) and added to the reaction mixture, followed by solid Pd₂DBA₃—CHCl₃ (8.4 mg, 0.008 mmol) and solid tris-(2,4,6-trimethoxyphenyl)phosphine(17 mg, 0.032 mmol). The reaction mixture was warmed immediately to RT in a water bath. The solution was stirred at RT until the enol triflate was consumed (TLC 70:30 ethyl acetate on SiO₂, or system indicated above). The reaction was worked up by pouring into H₂O and CH₂Cl₂. The organic fraction was extracted several times with water, backextracting the aqueous phases with CH₂Cl₂. The organic extracts were dried over Na₂SO₄, filtered and reduced i. vac. The product is recovered with quantities of N-methyl-2-pyrrolidinone. The product is partially purified by precipitation from N-methyl-2-pyrrolidinone solution with ∼30 volumes of ether and centrifugation. The partially purified yield is typically ∼74%. The yield is given over two steps for compound 18 below.

¹H NMR[400 MHz, d6 Acetone] 9.56 (s, 1H, exchangable imidazolium CH), 8.12 (d, 2H, 8.8 Hz), 8.04 (m, 1H), 7.87 (m, 2H), 7.71 (s, 1H), 7.56 (m, 4H), 5.30 (ABq, 2H, Δν69.6 Hz, J$_{AB}$ 14 Hz), 4.37 (dt, 1H, 7.3,1.3 Hz), 4.17 (m, 1H), 4.14 (s, 3H), 3.35 (m, 1H), 3.32 (AB of ABX system, 2H, Δν99.42 Hz, J$_{AB}$ 18.4 Hz, J$_{AX}$ 8.7 Hz, J$_{BX}$ 10.2 Hz), 1.28 (d, 3H, 6.26 Hz).

(5R,6S)-2-[3'-[3''-methyl-1''-imidazolium]phenyl]-6-[(1R)-1-hydroxyethyl]carbapen-2-em-3-carboxylate.18

17 ⟶

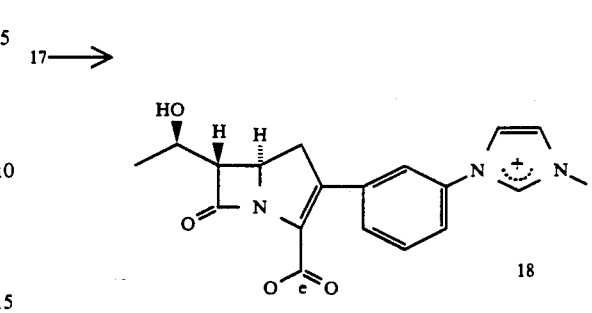

The carbapenem 17 was deprotected as for compound 10. The yield is typically 50%. Purification was by preparative chromatography on Analtech RPS-F 1 mm plates with 40% acetonitrile in water as eluent.

¹H NMR [400 MHz, D₂O] 9.21 (s, 1H, exchangable imidazolium CH), 7.85 (s, 1H), 7.63 (s, 1H), 7.58 (m, 2H), 7.54 (m, 2H), 4.34 (m, 1H), 4.28 (m, 1H), 4.02 (s, 3H), 3.56 (dd, 1H), 3.32 (AB of ABX system, 2H, Δν135.6 Hz, J$_{AB}$ 16.4 Hz, J$_{AX}$ 9.9 Hz, J$_{BX}$ 8.5 Hz), 1.32 (d, 3H, 4.6 Hz).

UV [H₂O, 0.1M MOPS pH=7] λ$_{max}$=302 nm, ε=9808, C=1.2.10⁻⁴.

EXAMPLE 3

1-[3',5'-bis-(trimethylstannyl)phenyl]-3-methylimidazolium triflate. 8

6 ⟶

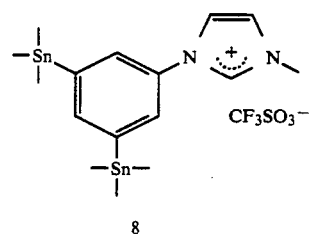

As for the imidazolium salt 7, the bis-stannane 6 was converted to its imidazolium salt 8 in ∼85% yield after recrystallization (two crops).

¹H NMR [d6 Acetone, 200 MHz] 9.61 (s, 1H), 8.20 (s, 1H), 7.96 (m, 1H), 7.89 (m, 1H), 7.86 (m, 2H), 4.19 (s, 3H), 0.37 (m, 18H).

p-Nitrobenzyl (5R,6S)-2-[3'-(trimethylstannyl)-5'-[3''-methyl-1''-imidazolium]phenyl]-6-[(1R)-1-hydroxyethyl]carbapen-2-em-3-carboxylate triflate. 19

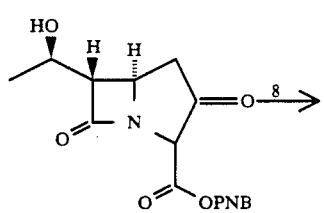

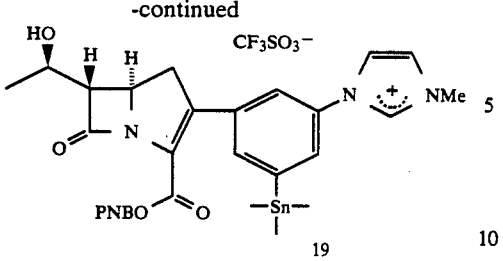

The carbapenem 19 was prepared as for compound 9. The crude extracts were used for the following destannylation step. The compound could be purified on an E. Merck Lobar RP-18 column with 70: 30 $CH_3CN$: water as eluent.

$^1$H NMR [400 MHz, d6 Acetone] 9.60 (s, 1H), 8.17 (m,1H), 8.15 (d, 2H, 8.8 Hz), 7.95 (m, 1H), 7.90 (m, 1H), 7.85 (m, 1H), 7.82 (m, 1H), 7.57 (d, 2H, 8.9 Hz), 5.32 (ABq, 2H, $\Delta\nu$42.3 Hz, $J_{AB}$14 Hz), 4.39 (m, 1H, 3.0, 8.6 Hz), 4.18 (s, 3H), 4.17 (m, 1H), 3.49 (AB of ABX system, 2H, $\Delta\nu$110.5 Hz, $J_{AB}$ 18.4 Hz, $J_{AX}$ 10, $J_{BX}$ 8.5 Hz), 3.42 (dd, 1H, 3.0, 7.0 Hz), 1.27 (d, 3H, 6.3 Hz), 0.34 (m, 9H).

(5R,6S)-2-[3'-iodo-5'-[3''-methyl-1''-imidazolium]-phenyl]-6-[(1R)-1-hydroxyethyl]carbapen-2-em-3-carboxylate. 21

19⟶

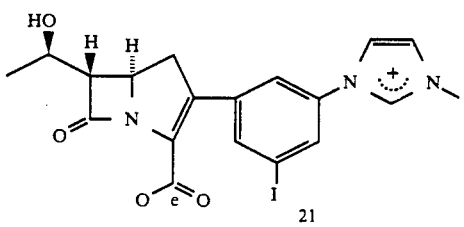

The carbapenem 19 was iodo-destannylated, and deprotected without purification. The carbapenem 19 (77 mg, 0.096 mmol) was dissolved in $CH_3CN$ (1 ml). Iodine (25.6 mg, 0.10 mmol) was dissolved in $CHCl_3$ (1 ml) and added to the carbapenem 29 at RT. The mixture was stirred for 10 min in the dark, and then poured into $CHCl_3$ and aq sodium thiosulfate. The organic fractions were washed two times with sodium thiosulfate solution, followed by brine and $H_2O$. The organic phases were dried with $Na_2SO_4$, filtered, and reduced i. vac. Crude extracts were used in the following deprotection.

The above crude product 20 was deprotected as for compound 10. The product carbapenem 21 was purified by chromatography on an E. Merck Lobar RP-18 column with 15% $CH_3CN$ in water as eluent. The yield over two steps was ~26%.

$^1$H NMR [400 MHz, $D_2O$] (imidazolium 2-CH exchanged out), 7.92 (t, 1H, 1.8 Hz), 7.88 (t, 1H, 1.4 Hz), 7.81 (d, 1H, 2.1 Hz), 7.62 (d, 1H, 2.1 Hz), 7.57 (t, 1H, 1.8 Hz), 4.30 (m, 1H), 4.26 (m, 1H), 4.01 (s, 3H), 3.54 (dd, 1H, 2.9, 5.9 Hz), 3.27 (AB of ABX system, 2H, $\Delta\nu$126 Hz, $J_{AB}$17 Hz, $J_{AX}$9.9, $J_{BX}$8.4 Hz), 1.31 (d, 3H, 6.5 Hz).

UV [$H_2O$, 0.1M MOPS pH=7] $\lambda_{max}$=306 nm, $\epsilon$=10828.

EXAMPLE 4

1-Amino-3-[3'-bromo-5'-(trimethylstannyl)phenyl-]imidazolium triisopropylbenzenesulfonate. 22

5⟶

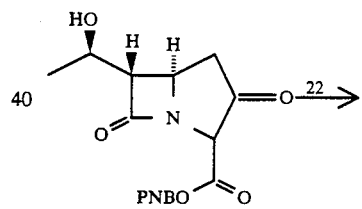

The imidazole 5 (400 mg, 1.04 mmol) was dissolved in $CH_2Cl_2$ (3 ml) with O-triisopropylbenzenesulfonyl hydroxylamine (310 mg, 1.04 mmol). The mixture was stirred five hours at RT. The reaction mixture was reduced i. vac., and purified by chromatography on an E. Merck Lobar RP-18 column with 9:1 $CH_3CN$:water. The solid 22 (473 mg, 67%) was recrystallized from ethyl acetate before use.

$^1$H NMR [400 MHz, $CDCl_3$] 9.98 (t, 1H, 1.7 Hz), 7.68 (m, 3H), 7.57 (d, 1H, 2.2 Hz), 7.26 (t, 1H, 2.0 Hz), 7.00 (s, 2H), 4.43 (spt, 2H, 6.9 Hz), 2.81 (spt, 1H, 6.9 Hz), 1.18 (d, 6H, 6.9 Hz), 1.15 (d, 12H, 6.8 Hz), 0.33 (m, 9H).

p-Nitrobenzyl (5R,6S)-2-[3'-bromo-5'-[3''-amino-1''-imidazolium]-phenyl]-6-[(1R)-1-hydroxyethyl]carbapen-2-em-3-carboxylate triisopropylbenzenesulfonate. 23

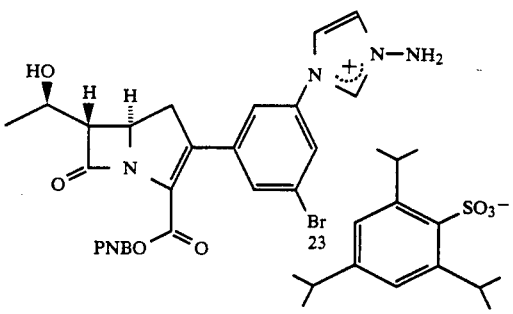

The carbapenem 23 was prepared as for compound 9. The crude product was deprotected as below without purification, or full characterization.

(5R,6S)-2-[3'-bromo-5'-[3''-amino-1''imidazolium]-phenyl]-6-[(1R)-1-hydroxyethyl]carbapen-2-em-3-carboxy late. 24

23⟶

-continued

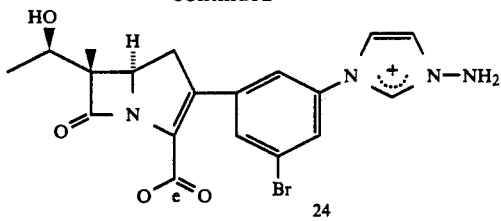

The carbapenem 23 was deprotected as for compound 10. The product 24 was purified by chromatography on an E. Merck Lobar RP-18 column with 15% CH3CN in water. The yield was 7%.

1H NMR [400 MHz, D2O] (imidazolium 2-CH exchanged out), 7.97 (d, 1H, 2.2 Hz), 7.80 (d, 1H, 1.8 Hz), 7.73 (s, 1H), 7.68 (d, 1H, 2.1 Hz), 7.59 (d, 1H, 1.8 Hz), 4.35 (m, 1H), 4.28 (m, 1H), 3.56 (dd, 1H, 2.8, 5.9 Hz), 3.30 (AB of ABX system, 2H, $\Delta\nu$124 Hz, $J_{AB}$ 17.1, $J_{AX}$ 9.9, $J_{BX}$ 8.6 Hz), 1.31 (d, 3H, 6.4 Hz).

UV [H2O, 0.1M MOPS pH=7] $\lambda_{max}$=306 nm, $\epsilon$=8159.

EXAMPLE 5

1-(3'-bromo-5'-cyanophenyl)imidazole. 25

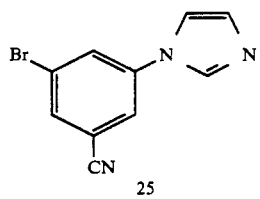

1-(3',5'-dibromophenyl)imidazole 4 (1 g, 3.38 mmol) was dissolved in N-methyl-2-pyrrolidinone (15 ml) with 1.25 eq CuCN (372 mg, 4.16 mmol) and heated to 150° C. When TLC (60:40 CCl4: ethyl acetate) showed no change in the comsumption of starting material (~22 HR). The reaction mixture was cooled and poured into a solution of 5 ml ethylenediamine in 100 ml water. This gave a blue solution and a dark brown precipitate. This solution was extracted with ethyl acetate three times, and the combined organic phases washed twice with ethylenediamine in water, then with brine. The organic phases were dried over Na2SO4, filtered and reduced i. vac. The crude oil was purified on SiO2 (62 g) with 60:40 CCl4: ethyl acetate as eluent. The yield of nitrile 25 is 49% and 30% of the starting dibromide is recovered.

1H NMR [400 MHz, d6 Acetone] 8.49 (s, 2H), 8.36 (s, 1H), 8.26 (s, 1H), 7.85 (s, 1H), 7.19 (s, 1H).

IR [CHCl3] 2950 cm$^{-1}$, 2240, 1575, 1492, 1310, 1250, 1180, 1105, 1055, 1000, 900, 865, 850, 810, 650.

1-[5'-Cyano-3'-(trimethylstannyl)phenyl]imidazole. 26

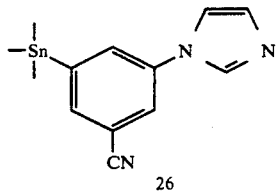

The stannane 26 was prepared as for compound 5. Four hundred milligrams of the nitrile yields 409 mg of the stannane 26, purified on SiO2 (50 g) with 55:45 CCl4: ethyl acetate as eluent. The yield is 80%.

1H NMR [200 MHz, CDCl3] 8.09 (brd, 1H), 7.74 (s, 1H), 7.68 (brd, 1H), 7.58 (brd, 1H), 7.26 (brd, 2H), 0.35 (m, 9H).

1-[5'-Cyano-3'-(trimethylstannyl)phenyl]-3-methylimida zolium triflate. 27

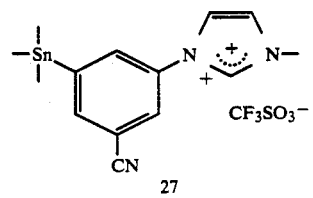

The imidazolium salt 27 was prepared as for compound 7. The crystalline residue was recrystallized from toluene containing 30% acetone. Recovery was typically 63% from the first crop.

1H NMR [300 MHz, d6 Acetone] 9.71 (s, 1H), 8.13 (d, 1H, 2.8 Hz), 8.04 (d, 1H, 2.4 Hz), 7.96 (d, 1H, 2.8 Hz), 7.9 (s, 1H), 7.78 (s, 1H), 4.13 (s, 3H), 0.36 (m, 9H).

p-Nitrobenzyl (5R, 6S)-2-[5'-cyano-3'[3''-methyl-1''-imidazolium]phenyl]-6-[(1R)-1-hydroxyethyl]carbapen-2-em-3-carboxylate. 28

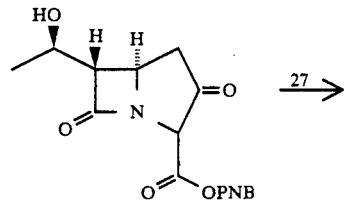

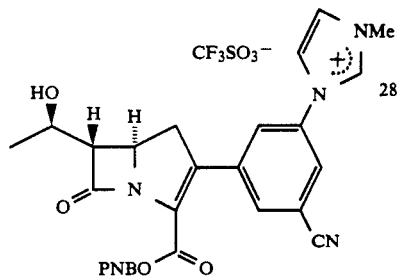

The bicyclic $\beta$-lactam (152 mg, 0.433 mmol) was dissolved in dry CH2Cl2 (5 ml) and cooled to −78° C. Diisopropylethyl amine (0.084 ml, 0.477 mmol) was added, and the solution stirred 5 min. Neat trifluoromethanesulfonic anhydride (0.081 ml, 0.477 mmol) was added dropwise, and the resulting solution stirred for 15 min at −78° C. to give a colorless suspension. The stannane 27 (215 mg, 0.433 mmol) was dissolved in dry CH2Cl2 (4 ml, rinsed 2 ml) and added to the reaction mixture, followed by solid Pd2DBA3—CHCl3 (45 mg, 0.043 mmol) and solid Et4NCl—(H2O)$_x$ (72 mg, 0.433 mmol). The reaction mixture was immediately warmed to room temperature in a water bath. The solution was stirred at RT until the enol triflate was consumed (TLC 70:30 ethyl acetate: hexane). The reaction was worked up by pouring into a mixture of water and $CH_2Cl_2$ and acetonitrile (1:1). The aqueous fraction was extracted several times with $CH_2Cl_2/CH_3CN$. The organic extracts were dried over $Na_2SO_4$, filtered and reduced i. vac. The product is partially purified by precipitation from acetonitrile solution with ~30 volumes of ether and centrifugation. The partially purified yield is close to 100%.

$^1H$ NMR [400 MHz, d6 Acetone] 9.7 (s, 1H), 8.32 (s, 1H), 8.27 (s, 1H), 8.24 (s, 1H), 8.18 (d, 2H, 3 Hz), 8.1 (s, 1H), 8.0 (s, 1H), 7.65 (d, 2H, 3 Hz), 5.36 (ABq, 2H, $\Delta\nu$66.1 Hz, $J_{AB}$ 13.9 Hz), 4.42 (m, 1H), 4.3 (m, 1H), 4.2 (m, 1H), 3.6 (AB of ABX system, 2H, $\Delta\nu$80 Hz, $J_{AB}$ 10 Hz, $J_{AX}$ 5 Hz, $J_{BX}$ 4 Hz), 3.4 (d, 1H, 3 Hz), 1.27 (d, 3H, 6 Hz).

(5R,6S)-2-[5'-cyano-3'-(3"-methyl-1"-imidizolium)-phenyl]-6-[(1R)-1-hydroxyethyl]carbapen-2-em-3-carboxylate. 29

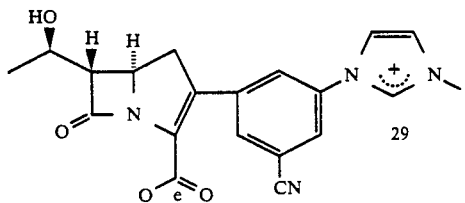

The carbapenem 28 was deprotected as for compound 10. The yield is typically 7%. The product was purified on an E. Merck RP-18 Lobar B column eluting with 90:10 water acetonitrile.

$^1H$ NMR [400 MHz, $D_2O$] 9.3 (s, 1H), 7.96 (s, 1H), 7.90 (s, 2H), 7.88 (d, 1H, 2 Hz), 7.66 (d, 1H, 1.8 Hz), 4.35 (m, 1H), 4.28 (m, 1H), 4.03 (s, 3H), 3.6 (m, 1H), 3.34 (AB of ABX system, 2H, $\Delta\nu$127.2, $J_{AB}$ 17 Hz, $J_{AX}$ 10.1 Hz, $J_{BX}$ 8.4 Hz), 1.32 (d, 3H, 6 Hz).

UV [$H_2O$, 0.1M MOPS pH=7] $\lambda_{max}$=309 nm, $\epsilon$=8537

EXAMPLE 6

(3-Iodo-5-methylsulfonylphenyl)isothiocyanate. 30

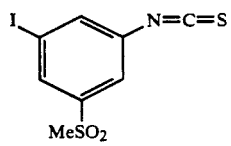

The isothiocyanate 30 was prepared as for compound 1. 1.40 g of aniline yields 1.06 g of isothiocyanate 30, (70%), which was used crude for the next step.

$^1H$ NMR [400 MHz, $CDCl_3$] 8.11 (s, 1H), 7.79 (s, 1H), 7.71 (s, 1H), 3.06 (s, 3H).

IR [$CHCl_3$] 1980 $cm^{-1}$, 1550, 1400, 1395, 1120.

N-(3-iodo-5-methylsulfonylphenyl)-N'-(2,2-dimethoxyethyl)thiourea 31

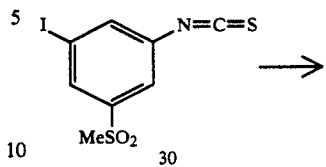

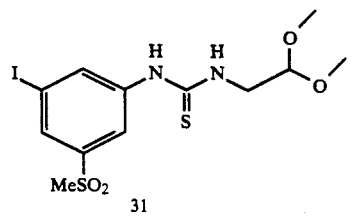

2,2-Dimethoxyethyl amine (0.245 ml, 236 mg, 2.25 mmol) was dissolved in absolute ethanol (8 ml). Crude isothiocyanate 30 (760 mg, 2.25 mmol) was added, and the mixture heated to reflux. When TLC (4:1 hexane ethyl acetate, $SiO_2$) indicates consumption of starting material (30 min), the mixture is allowed to cool to RT. The reaction mixture is reduced i. vac. and the product is purified on $SiO_2$ (44 g) using 4:1 $CH_2Cl_2$:ethyl acetate as eluent. The yield is 90%.

$^1H$ NMR [400 MHz, $CDCl_3$] 8.72 (brd, 1H), 8.1 (s, 1H), 7.92 (s, 1H), 7.85 (brds, 1H), 6.95 (brd, 1H), 4.51 (s, 1H), 3.82 (s, 2H), 3.4 (s, 6H), 3.05 (s, 3H).

IR [$CHCl_3$] 3640 $cm^{-1}$, 2960, 1685, 1570, 1440, 1295, 1130, 1115, 1080, 945.

1-(3'-Iodo-5'-methylsulfonylphenyl)imidazole. 33

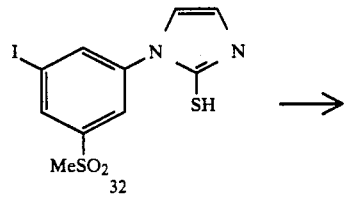

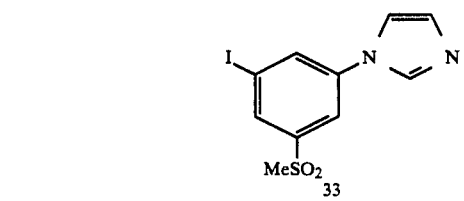

The imidazole 33 was prepared as for compound 4. The crude product was purified by recrystallization from acetone. The yield was 74% from two crops.

mercaptoimidazole 32

$^1H$ NMR [400 MHz, d6 Acetone] 9.58 (s, 1H), 8.35 (s, 1H), 8.25 (s, 1H), 7.42 (m, 1H), 7.22 (m, 1H), 3.25 (s, 3H).

IR [$CHCl_3$] 3650 $cm^{-1}$, 1555, 1450, 1420, 1270, 1115, 1080, 945.

imidazole 33

¹H NMR [400 MHz, d6 Acetone] 8.38 (s, 1H), 8.30 (s, 1H), 8.2 (s, 1H), 8.15 (s, 1H), 7.8 (s, 1H), 7.15 (s, 1H), 3.27 (s, 3H).

1-[5'-Methylsulfonyl-3'-(trimethylstannyl)phenyl-]imidazole. 34

33⟶

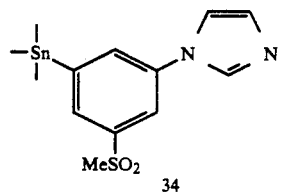

34

The stannane 34 is prepared as for compound 5. 104 mg of imidazole 33 yields 110 mg of stannane 34, 95%. The crude oil was purified on SiO₂ with 4:1 ethyl acetate CCl₄ as eluent.

¹H NMR [200 MHz, d6 Acetone] 8.3 (s, 1H), 8.15 (d, 1H, 2 Hz), 8.1 (s, 1H), 8.05 (d, 1H, 2 Hz), 7.76 (s, 1H), 7.2 (s, 1H), 3.22 (s, 3H), 0.42 (m, 9H).

1-[5'-Methylsulfonyl-3'-(trimethylstannyl)phenyl]-3-methylimidazolium triflate. 35

34⟶

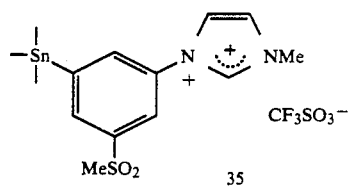

35

The triflate 35 was prepared as for compound 7. The crude product was recrystallized from toluene with 30% acetone. Recovery was 62% from the first crop.

¹H NMR [200 MHz, d6 Acetone] 9.8 (s, 1H), 8.4 (s, 1H), 8.4 (s, 1H), 8.3 (s, 1H), 8.24 (s, 1H), 8.04 (s, 1H), 4.25 (s, 3H), 3.25 (s, 3H), 0.45 (m, 9H).

p-Nitrobenzyl (5R, 6S)-2-[3'-methylsulfonyl-5'-(3''-methyl-1'-imidazolium]-phenyl)-6-[(1R)-1-hydroxyethyl]carbapen-2-em-3-carboxylate triflate. 36

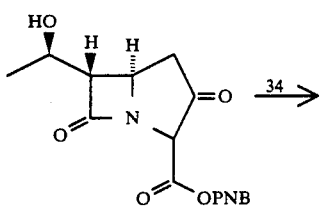

-continued

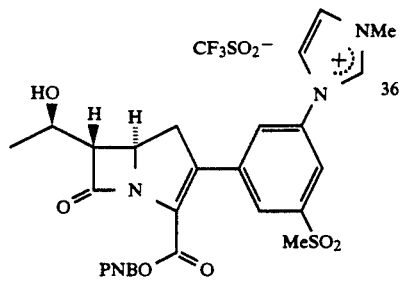

36

The carbapenem 36 was prepared as for compound 28. The product was deprotected without purification. Partial ¹H NMR [400 MHz, d6 Acetone] 9.75 (s, 1H), 8.31 (d, 2H, 8 Hz), 7.64 (d, 2H, 8.4 Hz), 5.35 (ABq, 2H, $\Delta\nu$45 Hz, $J_{AB}$ 13.8 Hz), 4.43 (m, 1H), 4.19 (s, 3H), ~3.6 (AB of ABX system (partially obscured), 2H, $\Delta\nu$~96.2, $J_{AB}$ 12 Hz, $J_{BX}$ 8.34), 3.51 (dd, 1H), 3.2 (s, 3H), 1.27 (d, 3H, 6.2 Hz).

(5R,6S)-2-[3'-methylsulfonyl-5'-(3''-methyl-1''-imidazolium)phenyl]-6-[(1R)-1-hydroxyethyl]carbapen-2-em-3-carboxylate. 37

36⟶

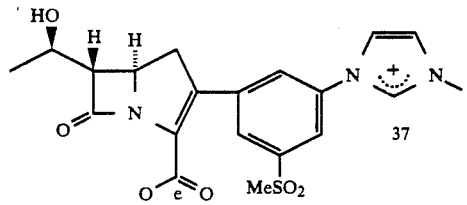

37

The carbapenem 36 was deprotected as for compound 29. The yield is 11%. The product was purified on an E. Merck RP-18 Lobar B column eluting with 8% acetonitrile in water.

¹H NMR [400 MHz, D₂O] ~9.2 (imidazolium C₂ H exchanged out), 8.13 (s, 1H), 8.09 (s, 1H), 7.96 (s, 1H), 7.94 (s, 1H), 7.68 (s, 1H), 4.36 (m, 1H), 4.28 (m, 1H), 4.04 (s, 3H), 3.61 (dd, 1H), 3.38 (AB of ABX system, 2H, $\Delta\nu$ 125.6 Hz, $J_{AB}$ 16.9 Hz, $J_{AX}$ 9.9 Hz, $J_{BX}$ 8.4 Hz), 3.34 (s, 3H), 1.33 (d, 3H, 6.23 Hz).

UV [H₂O, 0.1M MOPS pH=7] $\lambda_{max}$=311 nm, $\epsilon$=8629.

EXAMPLE 7

1-(3'-trimethylstannyl-5'-bromophenyl)-3-(3-hydroxypropyl) imidazolium triflate 38.

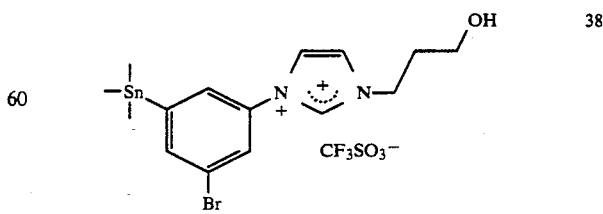

38

Lutidine (129 ml, 1.1 mmol) was dissolved in CH₂Cl₂ (2 ml) with 3-(t-butyldimethylsilyloxy)-1-propanol (207 mg, 1.1 mmol), and the solution cooled to −78° C. Neat trifluoromethanesulfonic anhydride (183 ml, 1.1 mmol) was added. The mixture was stirred 15 min. The stannane 5 (350 mg, 0.9 mmol) was dissolved in $CH_2Cl_2$ (3 ml) and added to the cold mixture. The mixture was allowed to come to RT and stirred overnight. The reaction mixture was diluted with $H_2O$ and extracted with $CH_2Cl_2$. Stirring the two phase mixture with $H_2O$ for several hours before extraction yields mostly the desilylated product, if desired. The dried and reduced organic extracts were purified on $SiO_2$ with 70:30 $CH_2Cl_2$ acetonitrile as eluent. Various mixtures of silylated and desilylated products were obtained, with a typical total yield of 80%.

$^1$H NMR [200 MHz, d6 Acetone] 9.72 (m, 1H), 8.29 (t, 1H, 1.95 Hz), 8.06 (m, 1H), 8.00 (m, 2H), 7.90 (m, 1H), 4.61 (t, 2H, 7.0 Hz), 3.69 (q, 2H, 5.3 Hz), 2.23 (m, 2H), 0.40 (m, 9H).

p-Nitrobenzyl (5R, 6S)-2-[5'-bromo-3'-(3''-[3-hydroxypropyl]-1''-imidazolium)phenyl]-6-[(1R)-1-hydroxyethyl]carbapen-2-em-3-carboxylate triflate. 39

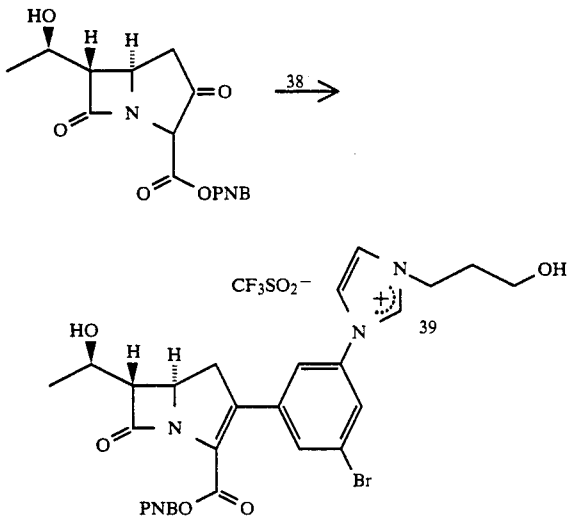

The carbapenem 39 was prepared and partially purified as for compound 28. The yield of partially purified material was good.

1H NMR [400 MHz, CD$_3$CN] 9.10 (s, 1H), 8.23 (d, 2H, 8.8 Hz), 7.86 (m, 1H), 7.83 (m, 2H), 7.72 (m, 2H), 7.56 (d, 2H, 8.8 Hz), 5.36 (ABq, 2H, $\Delta\nu$ 42.9 Hz, $J_{AB}$ 13.6 Hz), 4.46 (t, 2H, 6.95 Hz), 4.42 (m, 1H), 4.23 (m, 1H), 3.70 (q, 2H, 5.9 Hz), 3.52 (m, 1H), 3.44 (AB of ABX, partially obscured. 2H, $\Delta\nu \sim$50Hz, $J_{AB}$ 18 Hz, $J_{AX}$ 8.4 Hz, $J_{BX}$ 10.2 Hz), 2.19 (m, 2H), 1.34 (d, 3H, 6.4 Hz).

(5R, 6S)-2-[3'-bromo-5'-(3''-[3-hydroxypropyl]-1''-imidazolium)phenyl]-6-[(1R)-1-hydroxyethyl]carbapen-2-em-3-carboxylate. 40

39 ⟶

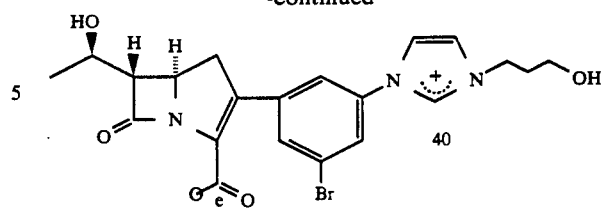

The carbapenem 39 was deprotected as for compound 10. The product 40 was purified by chromatography on an E. Merck Lobar RP-18 column with 12% $CH_3CN$ in water. The yield was ~20% over two steps.

$^1$H NMR [400 MHz, $D_2O$] 9.32 (imidazolium 2-CH partially exchanged), 7.87 (m, 1H), 7.78 (s, 1H), 7.73 (m, 2H), 7.58 (s, 1H), 4.44 (t, 2H, 7.3 Hz), 4.33 (m, 1H), 4.28 (m, 1H), 3.70 (t, 2H, 6.2 Hz), 3.56 (dd, 1H, 2.8, 5.9 Hz), 3.30 (AB of ABX system, 2H, $\Delta\nu$ 124 Hz, $J_{AB}$ 16.9, $J_{AX}$ 9.9, $J_{BX}$ 8.6 Hz), 2.19 (m, 2H), 1.31 (d, 3H, 6.4 Hz).

UV [$H_2O$, 0.1M MOPS pH=7] $\lambda_{max}$=307 nm, $\epsilon$=10221.

What is claimed is:

1. A compound of the formula:

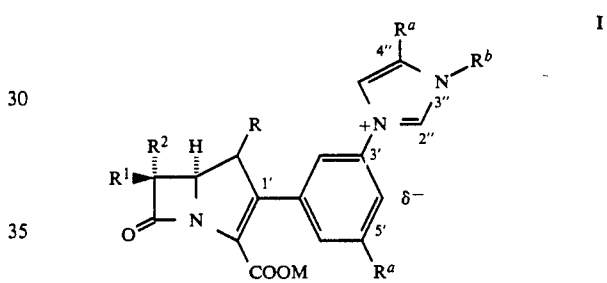

wherein:
R is H or $CH_3$;
$R^1$ and $R^2$ are independently H, $CH_3$—, $CH_3CH_2$—, $(CH_3)_2CH$—, $HOCH_2$—, $CH_3CH(OH)$—, $(CH_3)_2C(OH)$—, $FCH_2CH(OH)$—, $F_2CHCH(OH)$—, $F_3CCH(OH)$—, $CH_3CH(F)$—, $CH_3CF_2$—, or $(CH_3)_2C(F)$—;
$R^b$ is H, —$NH_2$, $C_1$-$C_4$alkyl, —($C_1$-$C_4$alkyl)-OH or (phenyl)$C_1$-$C_4$alkyl-;
$R^a$ are independently selected from the group consisting of hydrogen and the radicals set out in a), b), c) below,
a) a trifluoromethyl group: —$CF_3$;
b) a halogen atom: —Br, —Cl, —F, or —I;
c) $C_1$-$C_4$ alkoxy radical: —$OC_{1-4}$ alkyl, wherein the alkyl is optionally mono-substituted by $R^q$, where
$R^q$ is a member selected from the group consisting of —OH, —$OCH_3$, —CN, —$C(O)NH_2$, —OC(O)$NH_2$, CHO, —OC(O)N($CH_3$)$_2$, —$SO_2NH_2$, —$SO_2N(CH_3)_2$, —$SOCH_3$, —$SO_2CH_3$, —F, —$CF_3$, —COO$M^a$ (where $M^a$ is hydrogen, alkali metal, methyl or phenyl), tetrazolyl (where the point of attachment is the carbon atom of the tetrazole ring and one of the nitrogen atoms is monosubstituted by $M^a$ as defined above) and —$SO_3M^b$ (where $M^b$ is hydrogen or an alkali metal);
d) a hydroxy group: —OH;
e) a carbonyloxy radical: —O(C=O)$R^s$, where $R^s$ is $C_{1-4}$ alkyl or phenyl, each of which is optionally mono-substituted by $R^q$ as defined above or tri-substituted with —F;

f) a carbamoyloxy radical: —O(C=O)N($R^y$)$R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)— or —S(O)$_2$— to form a ring (where the ring is optionally mono-substituted with Rq as defined above);

g) a sulfur radical: —S(O)$_n$—$R^s$ where n=0-2, and $R^s$ is defined above;

h) a sulfamoyl group: —SO$_2$N($R^y$)$R^z$ where $R^y$ and $R^z$ are as defined above;

i) azido: N$_3$ j) a formamido group: —N($R^t$)(C=O)H, where $R^t$ is H or $C_{1-4}$ alkyl, and the alkyl thereof is optionally mono-substituted by $R^q$ as defined above;

k) a ($C_1$-$C_4$ alkyl)carbonylamino radical: —N($R^t$)(C=O)$C_{1-4}$ alkyl, where $R^t$ is as defined above, and the alkyl group is also optionally mono-substituted by $R^q$ as defined above;

l) a ($C_1$-$C_4$ alkoxy) carbonylamino radical: —N($R^t$)(C=O)O$C_{1-4}$ alkyl, where $R^t$ is as defined above, and the alkyl group is also optionally mono-substituted by $R^q$ as defined above;

m) a ureido group: —N($R^t$)(C=O)N($R^y$)$R^z$ where $R^t$, $R^y$ and $R^z$ are as defined above;

n) a sulfonamido group: —N($R^t$)SO$_2$$R^s$, where $R^s$ and $R^t$ are as defined above;

o) a cyano group: —CN;

p) a formyl or acetalized formyl radical: —(C=O)H or —CH(OCH$_3$)$_2$;

q) ($C_1$-$C_4$ alkyl)carbonyl radical wherein the carbonyl is acetalized: —C(OCH$_3$)$_2$$C_{1-4}$ alkyl, where the alkyl is optionally mono-substituted by $R^q$ as defined above;

r) carbonyl radical: —(C=O)$R^s$, where $R^s$ is as defined above;

s) a hydroximinomethyl radical in which the oxygen or carbon atom is optionally substituted by a $C_1$-$C_4$ alkyl group: —(C=NO$R^z$)$R^y$ where $R^y$ and $R^z$ are as defined above, except they may not be joined together to form a ring;

t) a ($C_1$-$C_4$ alkoxy)carbonyl radical: —(C=O)O$C_{1-4}$ alkyl, where the alkyl is optionally mono-substituted by $R^q$ as defined above;

u) a carbamoyl radical: —(C=O)N($R^y$)$R^z$ where $R^y$ and $R^z$ are as defined above;

v) an N-hydroxycarbamoyl or N($C_1$-$C_4$ alkoxy)-carbamoyl radical in which the nitrogen atom may be additionally substituted by a $C_1$-$C_4$ alkyl group: —(C=O)—N(O$R^y$)$R^z$ where $R^y$ and $R^z$ are as defined above, except they may not be joined together to form a ring;

w) a thiocarbamoyl group: —(C=S)N($R^y$)($R^z$) where $R^y$ and $R^z$ are as defined above;

x) carboxyl: —COO$M^b$, where $M^b$ is as defined above;

y) thiocyanate: —SCN;

z) trifluoromethylthio: —SCF$_3$;

aa) tetrazolyl, where the point of attachment is the carbon atom of the tetrazole ring and one of the nitrogen atoms is mono-substituted by hydrogen, an alkali metal or a $C_1$-$C_4$ alkyl optionally substituted by $R^q$ as defined above;

ab) an anionic function selected from the group consisting of: phosphono [P=O(O$M^b$)$_2$]; alkylphosphono {P=O(O$M^b$)—[O($C_1$-$C_4$ alkyl)]}; alkylphosphinyl [P=O(O$M^b$)—($C_1$-$C_4$alkyl)]; phosphoramido [P=O(O$M^b$)N($R^y$)$R^z$ and P=O(O$M^b$)NH$R^x$]; sulfino (SO$_2$$M^b$); sulfo (SO$_3$$M^b$); acylsulfonamides selected from the structures CONM$^b$SO$_2$$R^x$, CONM$^b$SO$_2$N($R^y$)$R^z$, SO$_2$NM$^b$CON($R^y$)$R^z$; and SO$_2$NM$^b$CN, where $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;

ac) $C_5$-$C_7$ cycloalkyl group in which one of the carbon atoms in the ring is replaced by a heteroatom selected from O, S, NH or N($C_1$-$C_4$ alkyl) and in which one additional carbon atom may be replaced by NH or N($C_1$-$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2$-$C_4$ alkenyl radical, optionally mono-substituted by one of the substituents a) to ac) above and phenyl which is optionally substituted by $R^q$ as defined above;

ae) $C_2$-$C_4$ alkynyl radical, optionally mono-substituted by one of the substituents a) to ac) above;

af) $C_1$-$C_4$ alkyl radical;

ag) $C_1$-$C_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from —S— and N$R^t$ (where $R^t$ is as defined above) and one of the saturated carbon atoms of the oxazolidinone ring is optionally mono-substituted by one of the substituents a) to ag) above;

M is:

i) a pharmaceutically acceptable esterifying group or removable carboxyl protecting group; or ii) absent, leaving COO$^-$; and $\delta^-$ is a counterion which is selected from I$^-$, Cl$^-$, CH$_3$SO$_3$$^-$, CH$_3$(C$_6$-H$_4$)SO$_3$$^-$, CF$_3$SO$_3$$^-$, triisopropylbenzene sulfonate; provided that $\delta^-$ is not present when M is absent.

2. The compound of claim 1 wherein $R^1$ is hydrogen and $R^2$ is (R)—CH$_3$CH(OH)— or (R)—CH$_3$CH(F)—.

3. The compound of claim 2 wherein $R^a$ in the 4''-position of said N-imidazoliumphenyl is hydrogen.

4. A compound according to claim 2 wherein $R^a$ other than hydrogen is selected from the group consisting of:

—OCH$_3$       —OCH$_2$CO$_2$CH$_3$

-continued

| | |
|---|---|
| —OCH₂CH₂OH | —CF₃ |
| —F | —Cl |
| —Br | —I |
| —OH | —OCOCH₃ |
| —OCONH₂ | —SCH₃ |
| —SOCH₃ | —SO₂CH₃ |
| —SCH₂CH₂OH | —SOCH₂CH₂OH |
| —SO₂NH₂ | —SO₂N(CH₃)₂ |
| —NHCHO | —NHCOCH₃ |
| —NHCO₂CH₃ | —NHSO₂CH₃ |
| —CN | —CHO |
| —COCH₃ | —COCH₂OH |
| —CH=NOH | —CH=NOCH₃ |
| —CH=NOCH₂CO₂CH₃ | —CH=NOCMe₂CONH₂ |
| —CH=NOCMe₂CO₂Me | —CO₂CH₂CH₂OH |
| —CONH₂ | —CONHCH₃ |
| —CON(CH₃)₂ | —CONHCH₂CN |
| —CONHCH₂CONH₂ | —CONHCH₂CO₂CH₃ |
| —CONHOH | —CONHOCH₃ |
| —tetrazolyl | —CO₂CH₃ |
| —SCF₃ | —CONHSO₂Ph |
| —CONHSO₂NH₂ | —SO₂CF₃ |
| —SO₂NHCN | —SO₂NHCONH₂ |
| —CH=CHCN | —CH=CHCONH₂ |
| —CH=CHCO₂CH₃ | —C≡C—CONH₂ |
| —C≡C—CN | —CH₂OH |
| —CH₂N₃ | —CH₂CO₂CH₃ |
| —SO₂CH₂CH₂OH | —CH₂I and |
| —SCH₂CONH₂. | |

5. A compound selected from the group consisting of:

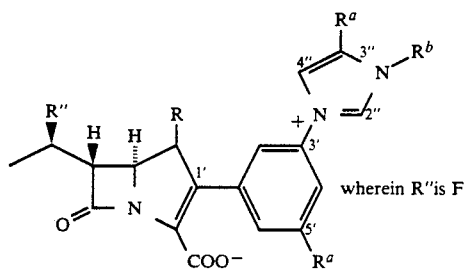

wherein R″ is F or OH, R is H or Me and $R^a$ and $R^b$ are:

| # | $R^b$ | $R^a$ | $R^a$ position |
|---|---|---|---|
| 1 | —CH₃ | —H | — |
| 2 | —CH₃ | —OCH₃ | 5′ |
| 3 | —CH₃ | —OCH₂CO₂CH₃ | 5′ |
| 4 | —CH₃ | —OCH₂CH₂OH | 5′ |
| 5 | —CH₃ | —CF₃ | 5′ |
| 6 | —CH₃ | —F | 5′ |
| 7 | —CH₃ | —Cl | 5′ |
| 8 | —CH₃ | —Br | 5′ |
| 9 | —NH₂ | —Br | 5′ |
| 10 | —(CH₂)₃OH | —Br | 5′ |
| 11 | —CH₃ | —I | 5′ |
| 12 | —CH₃ | —OH | 5′ |
| 13 | —CH₃ | —OCOCH₃ | 5′ |
| 14 | —CH₃ | —OCONH₂ | 5′ |
| 15 | —CH₃ | —SCH₃ | 5′ |
| 16 | —CH₃ | —SOCH₃ | 5′ |
| 17 | —CH₃ | —SO₂CH₃ | 5′ |
| 18 | —CH₃ | —SCH₂CH₂OH | 5′ |
| 19 | —CH₃ | —SOCH₂CH₂OH | 5′ |
| 20 | —CH₃ | —SCH₂CONH₂ | 5′ |
| 21 | —CH₃ | —SO₂NH₂ | 5′ |
| 22 | —CH₃ | —SO₂N(CH₃)₂ | 5′ |
| 23 | —CH₃ | —NHCHO | 5′ |
| 24 | —CH₃ | —NHCOCH₃ | 5′ |
| 25 | —CH₃ | —NHCO₂CH₃ | 5′ |
| 26 | —CH₃ | —NHSO₂CH₃ | 5′ |
| 27 | —CH₃ | —CN | 5′ |
| 28 | —CH₃ | —CHO | 5′ |
| 29 | —CH₃ | —COCH₃ | 5′ |
| 30 | —CH₃ | —COCH₂OH | 5′ |
| 31 | —CH₃ | —CH=NOH | 5′ |
| 32 | —CH₃ | —CH=NOCH₃ | 5′ |
| 33 | —CH₃ | —CH=NOCH₂CO₂CH₃ | 5′ |
| 34 | —CH₃ | —CH=NOCMe₂CO₂CH₃ | 5′ |
| 35 | —CH₃ | —CH=NOCMe₂CONH₂ | 5′ |
| 36 | —CH₃ | —CO₂CH₂CH₂OH | 5′ |
| 37 | —CH₃ | —CONH₂ | 5′ |
| 38 | —CH₃ | —CONHCH₃ | 5′ |
| 39 | —CH₃ | —CON(CH₃)₂ | 5′ |
| 40 | —CH₃ | —CONHCH₂CN | 5′ |
| 41 | —CH₃ | —CONHCH₂CONH₂ | 5′ |
| 42 | —CH₃ | —CONHCH₂CO₂CH₃ | 5′ |
| 43 | —CH₃ | —CONHOH | 5′ |
| 44 | —CH₃ | —CONHOCH₃ | 5′ |
| 45 | —CH₃ | -tetrazolyl | 5′ |
| 46 | —CH₃ | —CO₂CH₃ | 5′ |
| 47 | —CH₃ | —SCF₃ | 5′ |
| 48 | —CH₃ | —CONHSO₂Ph | 5′ |
| 49 | —CH₃ | —CONHSO₂NH₂ | 5′ |
| 50 | —CH₃ | —SO₂CF₃ | 5′ |
| 51 | —CH₃ | —SO₂NHCN | 5′ |
| 52 | —CH₃ | —SO₂NHCONH₂ | 5′ |
| 53 | —CH₃ | —CH=CHCN | 5′ |
| 54 | —CH₃ | —CH=CHCONH₂ | 5′ |
| 55 | —CH₃ | —CH=CHCO₂CH₃ | 5′ |
| 56 | —CH₃ | —C≡C—CONH₂ | 5′ |
| 57 | —CH₃ | —C≡C—CN | 5′ |
| 58 | —CH₃ | —CH₂OH | 5′ |
| 59 | —CH₃ | —CH₂CO₂CH₃ | 5′ |
| 60 | —CH₃ | —SO₂CH₂CH₂OH | 5′ |
| 61 | —CH₃ | —CH₂I | 5′ |
| 62 | —CH₂phenyl | —CONH₂ | 5′ |
| 63 | —NH₂ | —CONH₂ | 5′ |
| 64 | —CH₃ | —CONH₂ | 5′, 4″ |
| 65 | —CH₂phenyl | —CN | 5′ |
| 66 | —NH₂ | —CN | 5′ |
| 67 | —CH₃ | —CN | 5′, 4″ |
| 68 | —CH₂phenyl | —CHO | 5′ |
| 69 | —NH₂ | —CHO | 5′ |
| 70 | —CH₃ | —CHO | 5′, 4″ |
| 71 | —CH₂phenyl | —CH₂OH | 5′ |
| 72 | —NH₂ | —CH₂OH | 5′ |
| 73 | —CH₃ | —CH₂OH | 5′, 4″ |
| 74 | —CH₂phenyl | —S(O)CH₃ | 5′ |
| 75 | —NH₂ | —S(O)CH₃ | 5′ |
| 76 | —CH₃ | —S(O)CH₃ | 5′, 4″ |
| 77 | —CH₂phenyl | —SO₂CH₃ | 5′ |
| 78 | —NH₂ | —SO₂CH₃ | 5′ |
| 79 | —CH₃ | —SO₂CH₃ | 5′, 4″ |
| 80 | —CH₂phenyl | —I | 5′ |
| 81 | —NH₂ | —I | 5′ |
| 82 | —CH₃ | —I | 5′ |

6. A compound selected from the group consisting of:

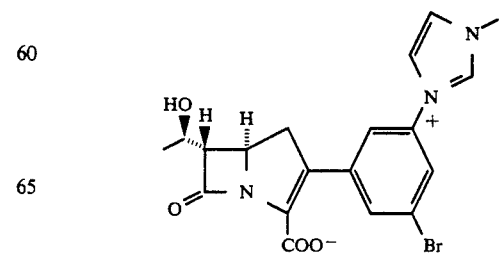

-continued
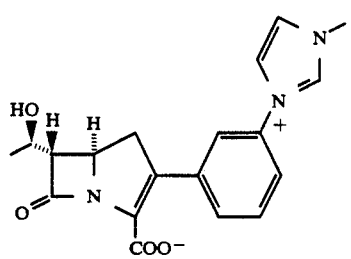
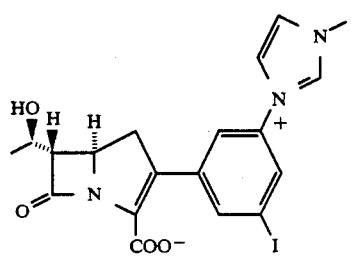
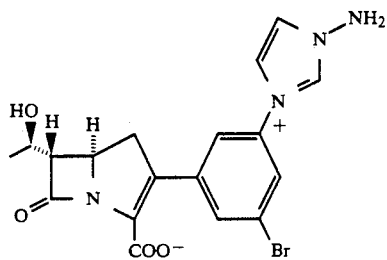
-continued
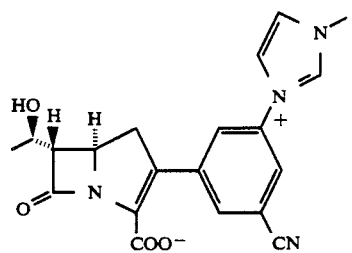
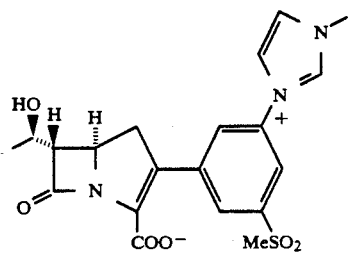
and
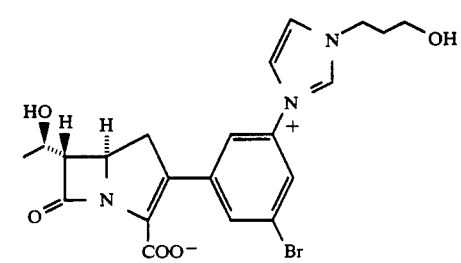
* * * * *